United States Patent [19]
Inoue

[11] Patent Number: 5,693,089
[45] Date of Patent: Dec. 2, 1997

[54] METHOD OF COLLAPSING AN IMPLANTABLE APPLIANCE

[76] Inventor: Kanji Inoue, 98-13, Miyazaki-cho Simogamo, Sakyo-ku, Kyoto-shi, Kyoto 606, Japan

[21] Appl. No.: 707,729

[22] Filed: Sep. 3, 1996

Related U.S. Application Data

[62] Division of Ser. No. 411,670, Apr. 12, 1995, abandoned.

[51] Int. Cl.$^6$ ............................................. A61F 2/06
[52] U.S. Cl. ........................... 623/1; 623/12; 606/198; 606/108
[58] Field of Search .................... 604/93, 247, 256; 606/198, 108; 623/1, 12

[56] References Cited

U.S. PATENT DOCUMENTS

| | | |
|---|---|---|
| 3,304,557 | 2/1967 | Polansky . |
| 4,313,231 | 2/1982 | Koyamada . |
| 4,872,874 | 10/1989 | Taheri . |
| 5,104,399 | 4/1992 | Lazarus . |
| 5,183,085 | 2/1993 | Timmermans . |
| 5,236,447 | 8/1993 | Kubo et al. . |
| 5,242,452 | 9/1993 | Inoue ........................ 606/108 |
| 5,290,305 | 3/1994 | Inoue . |
| 5,507,771 | 4/1996 | Gianturco . |
| 5,609,628 | 3/1997 | Keranen ........................ 623/12 |

FOREIGN PATENT DOCUMENTS

| | | |
|---|---|---|
| 0472731 | 3/1992 | European Pat. Off. . |
| 3-236836 | 10/1991 | Japan . |
| 91/12047 | 8/1991 | WIPO . |

*Primary Examiner*—Paul B. Prebilic
*Attorney, Agent, or Firm*—Banner & Witcoff, Ltd.

[57] ABSTRACT

This is a method of collapsing an artificial blood vessel A. The artificial blood vessel A comprises a pair of discrete end wire rings $10_1$, $10_2$, a tubular cover 7 made of a sheet of flexible, tensile material which connects the end wire rings $10_1$, $10_2$, and a plurality of intermediate wire rings 12 arranged spaced apart between the end wire rings $10_1$, $10_2$ and circumferentially fixed to the cover 7 by suturing or with adhesive.

A plurality of dividing points $41_1$, $43_1$ which bisect the circumference of the front end wire ring $10_1$ are pulled forward while the movement of the midpoints $42_1$, $44_1$ between the dividing points $41_1$, $43_1$ following the movement of the dividing points $41_1$, $43_1$ are restrained by the projections 18c on a tapered surface 18d of a funnelled tube 18 so as to fold the front end wire ring $10_1$ into a wavy shape, with the dividing points $43_1$, $43_1$ forming forwardly directed peaks and the midpoints $42_1$, $44_1$ forming the bottoms of forwardly directed valleys, and the dividing points of the front wire ring are pulled farther forward so as to fold the intermediate wire rings 12 and the rear end wire ring $10_2$ into a regular wavy shape having the same phase as that of the front wire ring $10_1$ by the effect of restraint by the tapered surface 18d and the projections 18c, thereby to collapse the artificial blood vessel A as a whole into a small size.

7 Claims, 30 Drawing Sheets

METHOD OF COLLAPSING AN IMPLANTABLE APPLIANCE

This application is a divisional of application Ser. No. 08/411,670, filed Apr. 12, 1995 now abandoned.

FIELD OF THE ART

This invention relates to appliances for medical treatment and, more particularly, to an appliance collapsible for insertion into a human organ and capable of resilient restoration (which will be referred to as "the appliance to be implanted" in this specification and claims), to a method of collapsing the appliance to be implanted, and to a device for introducing the collapsed appliance to be implanted into a catheter.

PRIOR ART

The artificial blood vessel is an example of the appliance to be implanted. At present, treatment of, for example, aortic aneurysm is conducted by implanting an artificial blood vessel. In particular, the portion of a blood vessel which has an aneurysm is removed by resection, and an artificial blood vessel is implanted in place of the resected portion and connected to the remaining blood vessel by suturing or the like.

The above-mentioned method of surgically implanting artificial blood vessels for treatment of aortic aneurysm, however, is highly dangerous. Especially, an emergency operation for treatment of a ruptured aneurysm has a low life-saving rate, and an operation of dissecting aortic aneurysm is difficult to conduct and has a high death rate.

Therefore, in order to treat these diseases without a surgical operation, a method has been developed of introducing into a catheter an appliance such as an artificial blood vessel in collapsed condition into a human organ such as a blood vessel, and transporting the appliance to a desired position such as an affected or constricted portion thereof, where the appliance is released so as to be expanded and implanted there with accuracy.

The appliance to be implanted comprises a pair of end wire rings and a frame mainly composed of connecting wires which connect the above-mentioned end wire rings. The appliance is pushed at the rear end wire ring into a catheter and transported to a desired organ in a human body. In order to transport the appliance, the force applied to the rear end wire ring should be transmitted to the front end wire ring. Therefore, it is indispensable that the frame should be made of comparatively strong metal and that the appliance should have the frame as an inevitable constructing element. If the above-mentioned frame is used, interference is likely to take place between the end wire rings and the frame and prevents the end wire ring from being folded, which makes it difficult to fold the end wire rings into a regular wavy shape. The difficulty in folding the end wire rings will make it difficult to collapse the whole appliance to be implanted into a small size.

As the end wire rings have an elastic limit, if a force exceeding the elastic limit is applied to the rings, the end wire rings folded for insertion into a catheter suffer plastic deformation so that the end wire rings may not be restored to a proper shape when released at an objective position in a human organ. The distortions caused by the plastic deformation may give rise to sliding resistance and prevent the appliance to be implanted from traveling in a catheter, thereby to make it difficult or impossible for the appliance to be transported to a desired position.

In addition, a frame, if used in the appliance to be implanted, is likely to hinder the appliance from being implanted in an appropriate shape into a human organ. Especially, in placing the appliance into a bent portion of a human organ, the frame may be deformed into a flat shape because different parts of the frame interfere with each other. Even if the appliance has been implanted, it may not be able to function as it is intended to. In the conventional frame, the wire of the wire rings provided at the opposite ends of the frame is exposed, so that the inner wall of a human organ may be scratched and damaged by the wire and blood is likely to leak out from the end wire rings because the rings are not adhered closely to the inner wall of the human organ.

Even though a check valve is provided at the outer end of a catheter whose front end has been inserted into the blood vessel of a human body beforehand, the check valve must be temporarily opened when the collapsed appliance is introduced into the catheter, thereby to cause a lot of bleeding. It is therefor desirable to provide means for preventing bleeding.

The present invention has been accomplished to solve the above-mentioned problems. The object of the invention is to develop an appliance of non-frame type, which can solve all of the above-mentioned problems.

DISCLOSURE OF THE INVENTION

The method of collapsing the appliance to be implanted in accordance with the invention is characterized by that the appliance to be implanted comprises a pair of discrete end wire rings, a tubular cover made of a sheet of flexible, tensile material which connects the above-mentioned end wire rings, and a plurality of intermediate wire rings arranged spaced apart between the above-mentioned end wire rings and circumferentially fixed to the above-mentioned cover by suturing or with adhesive; and that the method comprises the steps of; pulling forward the front end wire ring at a plurality of dividing points which equally divide the circumference of the front end wire ring while restraining the midpoints between each adjacent two dividing points by a tapered surface from moving forward following the forward movement of the dividing points, thereby to fold the front end wire ring into a wavy shape with the dividing points forming forwardly directed peaks and the midpoints forming the bottoms of forwardly directed valleys, and pulling the dividing points of the front wire ring farther forward thereby to fold the intermediate wire rings and the rear end wire ring into a wavy shape having the same phase as that of the front end wire ring by the effect of restraint with the tapered surface.

A loop for a pull string to be passed through may be formed at each of the dividing points on the front end wire ring so that a front pull string may be passed through each of the loops and pulled forward. In particular, a common pull string may advantageously be passed through a plurality of loops so that the dividing points may be gathered together by pulling the common front pull string. A funnelled guide tube whose bore diameter is gradually reduced toward its forward end may be used to gather the dividing points and the midpoints by pulling forward the dividing points on the front end wire ring of the appliance to be implanted inserted into the funnelled guide tube through its rear opening. In particular, resiliently deformable projections can be formed on the tapered inner surface of the funnelled guide tube so as to bring the midpoints into contact with the projections thereby to effectively restrain the midpoints from moving forward following the movement of the dividing points and cause the midpoints to approach to each other. The end wire rings can be circumferentially covered with elastic protective material.

The appliance to be implanted in accordance with the invention is characterized by that a pair of discrete end wire rings which are resiliently foldable are provided at opposite ends; that the end Wire rings are connected by only a tubular cover made of a sheet of flexible, tensile material; and that a plurality of intermediate wire rings are arranged between the above-mentioned end wire rings and fixed to the above-mentioned cover at appropriate points on the circumference thereof by suturing or with adhesive.

The flexible, tensile sheet may be made, for example, of warps extending in the axial direction of the appliance to be implanted woven with wefts extending in the circumferential direction thereof. The warps are made of mono-filament of polyester capable of keeping its shape and the wefts are made of multi-filament of polyester having waterproofness.

The tubular cover may be in the form of bellows. Especially, the end wire rings may advantageously be connected by restraining strings-so as to prevent the bellows from overstretching to exceed a given limit. The end wire rings can be circumferentially covered with an elastic protective material. Further, thorns can be provided on the circumference of at least one of the wire rings so as to stick into a human organ to be embedded therein. The thorns may be effectively formed by curving a wire into a loop, crossing the opposite end portions of the wire, and fixing the crossing point, thereby to form the opposite end portions into the thorns.

The device for introducing the appliance to be implanted in collapsed state into a catheter in accordance with the invention comprises an attachment having a flexible check valve which closes an open end thereof and fixed to an open end of a catheter, and a cartridge removably attachable to the above-mentioned attachment and having an open end closed by a flexible check valve and a front end portion connected to the above-mentioned catheter when the cartridge is attached to the attachment; and by that the check valve of the cartridge is pushed open to introduce the appliance to be implanted into the cartridge, and while the check valve of the cartridge is kept nearly closed, the front end portion of the cartridge is inserted into the catheter by pushing the check valve of the attachment open.

The bore diameter of the attachment of the catheter is made larger than that of the open end of the catheter, so that when the cartridge is attached, the bore of the front end portion of the cartridge may be smoothly connected to the open end of the catheter through the attachment of the catheter.

With the method of collapsing the appliance to be implanted in accordance with the invention, the operation of collapsing the appliance can be conducted with ease and accuracy. It is difficult to fold the front end wire ring into such a small size that can be contained in a catheter just by applying non-directional external force thereto. However, if the dividing points which equally divide the circumference of the front end wire ring are pulled forward with the midpoints provided between the dividing points being restrained by a tapered surface from moving forward following the dividing points, the front end wire ring is folded into a wavy shape with the midpoints serving as footholds and with the dividing points forming forwardly directed peaks and the midpoints forming the bottoms of forwardly directed valleys. After the front end wire ring has been bent, the intermediate and the rear end wire rings also are folded into a wavy shape having the same phase as that of the front end wire ring by pulling farther forward the dividing points on the front end wire ring to transmit the pulling force to the intermediate and the rear end wire rings through the tensile cover, and by simultaneously restraining the intermediate and the rear end wire rings by means of a tapered surface, thereby to collapse the whole appliance into a small size with ease.

What should especially be referred to is that the method of collapsing the appliance to be implanted in accordance with the invention is characterized by that a pair of end wire rings provided at the opposite ends of the appliance are connected by only a tubular cover which is made of a sheet of flexible, tensile material; and that the front end wire ring is pulled forward. The conventional method, in which the rear end portion of the appliance to be implanted is pushed to insert the appliance into a human organ, requires a relatively strong frame made mainly of connecting wire rings in order to transmit the force applied to the rear end of the appliance to the forward portion thereof. However, the invention is based on pulling the front end wire ring forward, thereby to make it possible to insert the appliance with ease even without a frame. In addition, the cover follows the movement of the wire rings being folded and is transformed into any desired shape, thereby to avoid interference between the wire rings and the frame. Consequently, by the method of collapsing the appliance in accordance with this invention it is possible to fold each of the wire rings into a wavy shape and to collapse the whole appliance into a small size with ease.

The operation of folding the wire rings is conducted with ease by forming loops for a pull string to be passed through at the dividing points on the front end wire ring and pulling forward a front pull string passed through the loops. In particular, a common front pull string passed through a plurality of loops is more effective to change the pulling force to a force to fold the wire rings because the dividing points are gathered toward each other.

In collapsing the appliance, a funnelled guide tube whose bore diameter is-gradually reduced in the forward direction may advantageously be used, so that the dividing points and midpoints of the wire rings are gathered toward each other as the appliance to be implanted is inserted farther into the funnelled tube, thereby to collapse the appliance as a whole into a small size. If projections resiliently deformable and engageable with the midpoints are formed on the tapered inner surface of the funnelled guide tube, the midpoints are urged toward each other by the counterforce from the projections, and a space is formed between the end wire rings and the funnelled guide tube, thereby effectively to prevent the appliance and the funnelled guide tube from closely contacting each other to increase sliding resistance therebetween so that the appliance cannot be moved in the guide tube.

Elastic protective material circumferentially covering the end wire rings is useful to prevent the appliance from being damaged when collapsed into a small size. If the wire ring is bent to such a degree that the elastic limit is exceeded, not only it becomes difficult for the ring to be restored to its original annular shape but also it becomes impossible to move the ring in a catheter due to the bent portion being caught in the catheter. However, if protective material is provided, the material disperses the tension which would otherwise be exerted locally on the dividing points when the points are strongly pulled, thereby to prevent tension from being applied locally to the dividing points so that the elastic limit is exceeded to bent the wire ring. The protective material prevents the front end wire ring from being plastically deformed, and provides it with a proper capability of resilient restoration to an annular shape and of traveling smoothly in a catheter, thereby to fold the front end wire ring into a regular wavy form.

The appliance having no frame, as mentioned above, properly functions as an artificial blood vessel. The appliance in accordance with the invention has a feature that the cover itself is tensile and is held by the wire rings at both ends and the intermediate wire rings at appropriate points thereof. Therefore, when the whole appliance is released from the state of being collapsed and each of the wire rings are resiliently restored to the annular shape, the cover is resiliently restored to its original proper tubular shape. The conventional appliance having a frame is likely to be deformed flatly because of mutual interference of the component parts when it is arranged in a bent portion of a human organ. However, the appliance of the invention having no frame can be transformed into any desired shape so as to conform to different shapes of a human organ.

A sheet woven with warps and wefts, in which the warps are made of mono-filament of polyester and the wefts are of multi-filament of polyester, makes the whole appliance flexible. In addition, the warps provide the cover of the appliance with tensile strength in the axial direction and a capability of keeping its shape, and the wefts make the sheet closely woven and increase its waterproofness.

If the sheet of the cover is in the form of bellows, the whole appliance is bent smoothly, thereby to improve the condition of the appliance when implanted into a human organ. If the sheet of the cover is in the form of bellows, restraining strings connecting the front and the rear end wire rings can prevent the bellows from stretching to such a degree that the elastic limit is exceeded to be flat.

The elastic protective material circumferentially covering the wire rings can prevent, as mentioned previously, not only the wire rings from being plastically deformed when folded into a small size but also the inner wall of a human organ from being damaged by direct contact with the wire rings. The protective material also acts as a seal to attach both ends of the appliance to be implanted tightly to the inner wall of a human body, thereby to effectively prevent leakage of blood through the ends of the appliance when implanted.

When thorns are provided projecting from the wire rings, they stick into the inner wall of a human organ to be embedded therein so that the whole appliance is fixed to the human organ. Therefore, the thorns effectively prevent the appliance from being displaced or even carried by blood flow downstream in a blood vessel. The thorns are formed with ease by curving a wire into a loop, crossing both end portions of the wire, and fixing the crossed parts with a string or the like, even though the material of the wire is difficult to weld. The thorns thus formed reliably function as mentioned above for a long time.

In addition, with the device for introducing a collapsed appliance to be implanted into a catheter in accordance with the invention it is possible to introduce the appliance to be implanted smoothly into a catheter. In particular, the appliance to be implanted is inserted into the cartridge by pushing the check valve open as far as the appliance reaches a position at which it is almost completely contained in the cartridge. Before or after the insertion, the cartridge is attached to the attachment provided at the open end of the catheter, and then the appliance is pulled farther forward in that condition so as to be introduced into the catheter through the attachment. When the check valve in the attachment is opened, the check valve of the cartridge is closed, so that blood flowing into the cartridge is prevented from flowing outside the body through the cartridge without fail.

In addition, if the appliance is to be inserted directly into the catheter, the appliance cannot be inserted smoothly because of the catheter and the appliance being flexible, and the catheter is bent by the force applied to the appliance, thereby to block the passage through which the appliance is to be inserted or to make the catheter fragile. On the other hand, if the appliance is to be inserted into the catheter through the attachment and the cartridge, by making the attachment and the cartridge strong and of such a shape as to be handled with ease it is possible to solve the problem of the catheter being bent or otherwise deformed, thereby to enable the appliance to be introduced into the catheter smoothly and with ease. If the bore diameter of the attachment is made bigger than that of the catheter and the bore diameter of the front end of the cartridge is smoothly connected to that of the open end of the catheter when the cartridge is attached to the catheter, it is possible to prevent the appliance to be implanted from being temporarily swollen in the attachment and caught therein, and to introduce the appliance to be implanted deep into the catheter.

BEST MODES OF EMBODYING THE INVENTION

The invention will be described in detail with reference to the embodiments thereof shown in the accompanying drawings.

Figure 1:
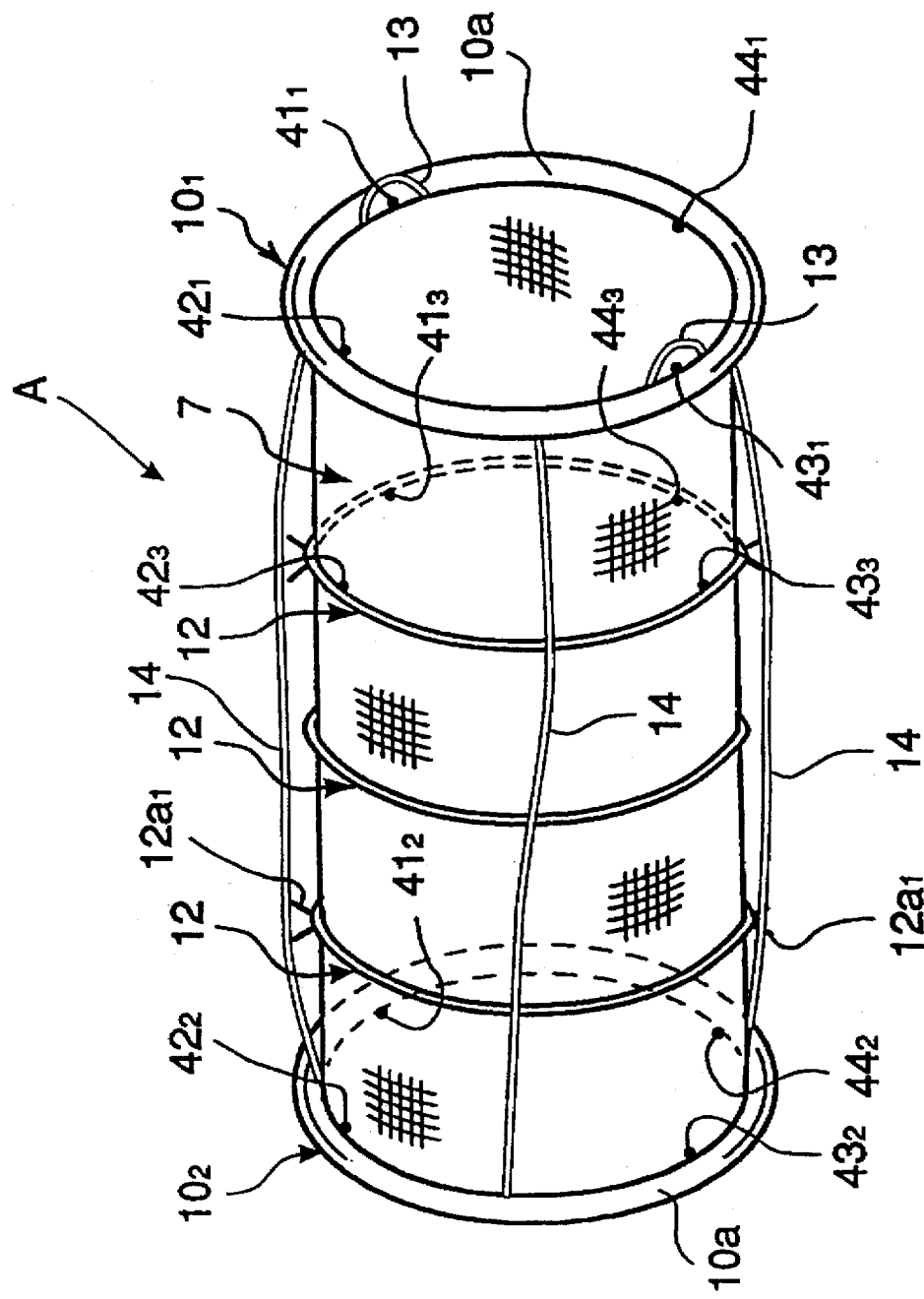
FIG. 1 is a perspective view of an artificial blood vessel used in one embodiment of the invention.

The artificial blood vessel A as the appliance to be implanted, which is collapsed by the method in accordance with this invention, comprises, as shown in FIG. 1, a cover 7, end wire rings $10_1$, $10_2$ and intermediate wire rings 12.

Figure 2:
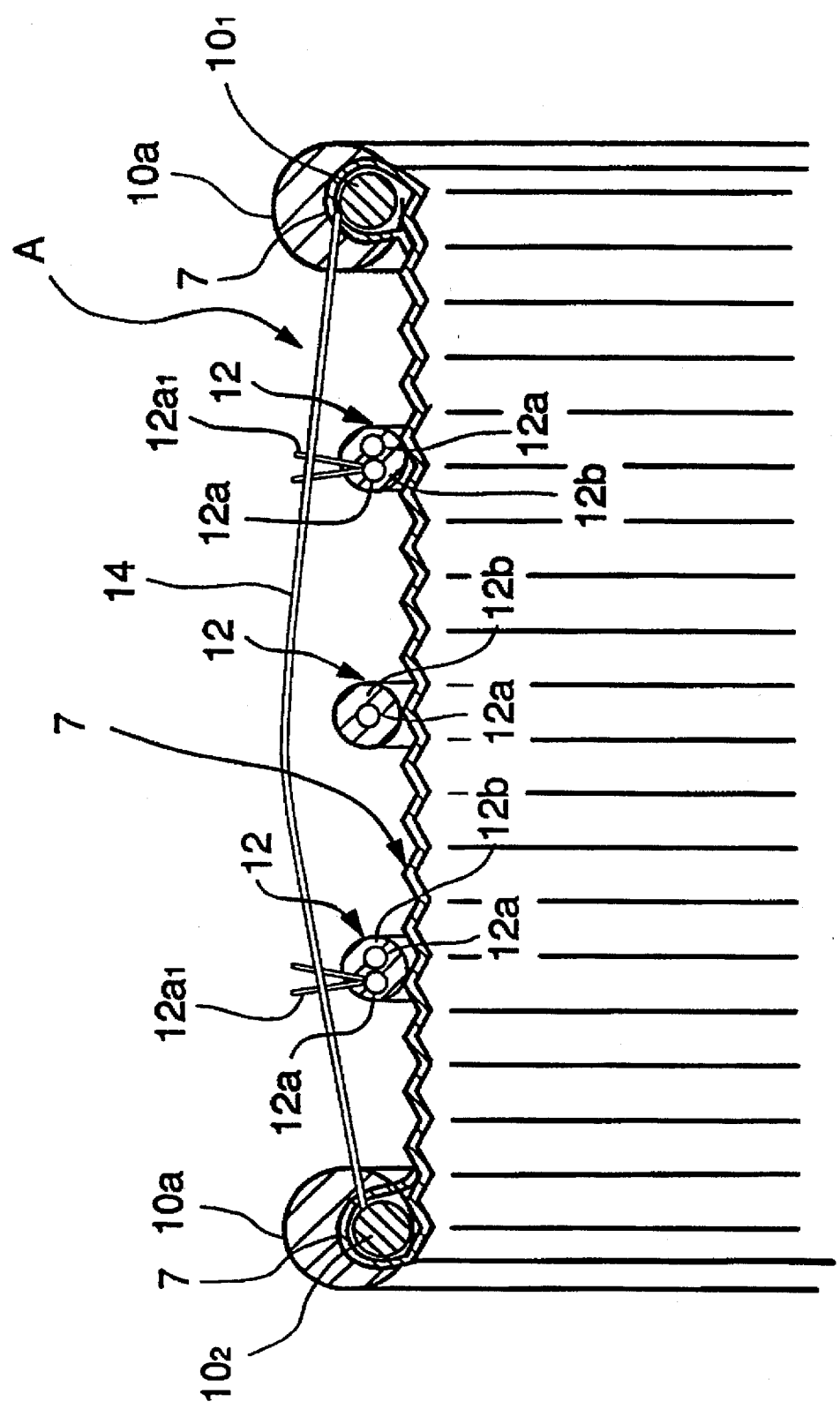
FIG. 2 is a vertical cross-sectional view of part of the artificial blood vessel.

The cover 7, as shown in FIG. 2, consists of a flexible, tensile sheet shaped into a tube of bellows, the diameter of which generally corresponds to the normal diameter of that portion of the human blood vessel at which the artificial blood vessel A is to be implanted. The sheet of the cover 7 is, for example, of warps extending in the axial direction of the artificial blood vessel A woven with wefts extending in the circumferential direction thereof, wherein the warps are of mono-filament made of polyester (about 15 denier) and the wefts are of multi-filament made of a plurality of superfine filaments (about 50 denier) interwoven. The cover 7 is coated, if necessary, with waterproof material, for example, collagen or albumin, to prevent leakage of blood.

The end wire rings $10_1$, $10_2$, whose inner diameter generally corresponds to that of the above-mentioned cover 7, are axially spaced apart and arranged face to face, and are fixed to the opposite ends of the cover 7 by suturing or with adhesive as shown in FIG. 2. The circumferences of the end wire rings $10_1$, $10_2$ are covered with protective braid members $10a$, which are closely fixed to the end wire rings $10_1$, $10_2$ at appropriate positions with thread, adhesive or the like.

The intermediate wire rings 12, which comprise, as shown in FIGS. 1 and 2, one or two wire rings $12a$ wrapped with protective film $12b$ made of cloth or the like, are arranged axially equidistantly between the end wire rings $10_1$ and $10_2$, and fixed to the cover 7 at appropriate positions on the circumference thereof with thread, adhesive or the like. The above-mentioned end wire rings $10_1$, $10_2$ and the intermediate wire rings 12 help keep the tubular shape of the cover 7. Thorns $12a_1$ are formed at two diametrically opposite positions on each of those two intermediate wire rings 12 each of which comprises two wire rings $12a$, so that the thorns $12a_1$ may stick into a human organ so as to be embedded therein. In particular, the wires $12a$ of the intermediate rings 12 as well as those of the end wire rings $10_1$, $10_2$ are made of Ti-Ni alloy or the like. The wires of Ti-Ni alloy have a high resilient restoring force, but are hard to weld. As the Ti-Ni alloy has the above-mentioned characteristic, the thorns $12a_1$ are formed by forming a length of wire $12a$ into a loop, whose opposite end portions are crossed so as to provide a pair of short lengths of wire projecting from the crossing point, which is tied with a string or the like, and the projecting end wire portions are bent to provide the thorns $12a_1$ on the ring. In the same manner, a pair of thorns $12a_1$ are provided on another ring formed of a length of wire $12a$. The two rings are arranged side by side, with the thorns $12a_1$ on one of the rings arranged diametrically opposite to the thorns $12a_1$ on the other ring. The two rings $12a$ are covered with a protective film $12b$, through which the thorns $12a_1$ project outside.

As shown in FIG. 1, let it be assumed here that the circumference of the front end wire ring $10_1$ to the first introduced into the catheter 8 is bisected by two points which will be referred to as the dividing points $41_1$, $43_1$, and the two midpoints between the two dividing points $41_1$, $43_1$ will be referred to as the midpoints $42_1$, $44_1$. On the circumference of the rear end wire ring $10_2$, those points whose phases are the same as the dividing points $41_1$, $43_1$ and the midpoints $42_1$, $44_1$ will be referred to as the points $41_2$, $43_2$ corresponding to the dividing points $41_1$, $43_1$ and the points $42_2$, $44_2$ corresponding to the midpoints $42_1$, $44_1$, respectively. On the circumference of the intermediate wire ring 12, those points whose phases are the same as the dividing points $41_1$, $43_1$ and the midpoints $42_1$, $44_1$ will be referred to as the points $41_3$, $43_3$ corresponding to the dividing points $41_1$, $43_1$ and the points $42_3$, $44_3$ corresponding to the midpoints $42_1$, $44_1$, respectively. As shown in FIG. 1, a pair of loops 13 of thread or the like are so formed that the centers thereof are positioned at the dividing points $41_1$, $43_1$ of the front end wire ring $10_1$. Restraining strings 14 bridge the end wire rings $10_1$ and $10_2$ so as to prevent the artificial blood vessel A from being stretched unnecessarily too much along the axis thereof.

In order to implant the artificial blood vessel A of the above-mentioned construction into a target organ of a human body, a device B for transporting artificial blood vessels (see FIG. 3) is used to transport the artificial blood vessel A to the target organ of the human body through the catheter 8 and a device C for introducing artificial blood vessels (see FIG. 4) is used to introduce the artificial blood vessel A into the catheter 8.

Figure 3:
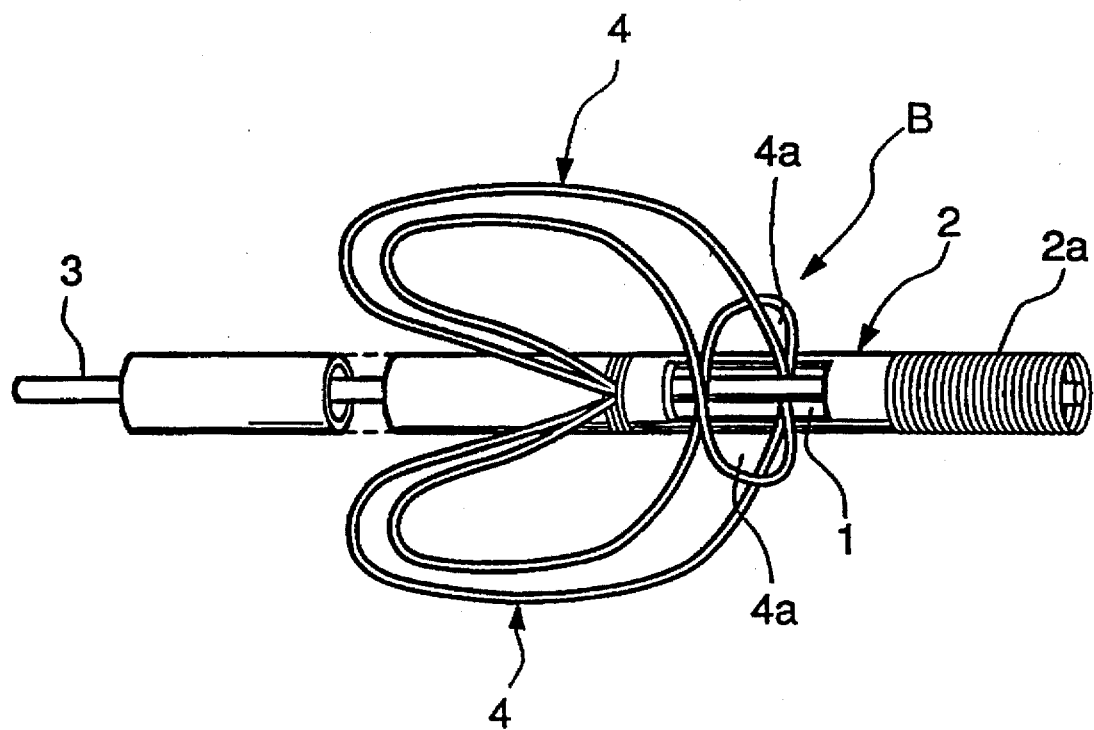
FIG. 3 is a perspective view of a device for transporting the artificial blood vessel, used in the embodiment.

The device B for transporting artificial blood vessels, as shown in FIG. 3, comprises a flexible metallic tube 2 whose front end portion is connected to a helical spring $2a$ for guiding, a side window 1 formed adjacent the front end of the tube 2, a pair of strings 4 having both their ends fixed to the tube 2 adjacent the side window 1 and their middle portions formed into loops $4a$, and a length of wire 3 slidably inserted into the tube 2.

Figure 4:
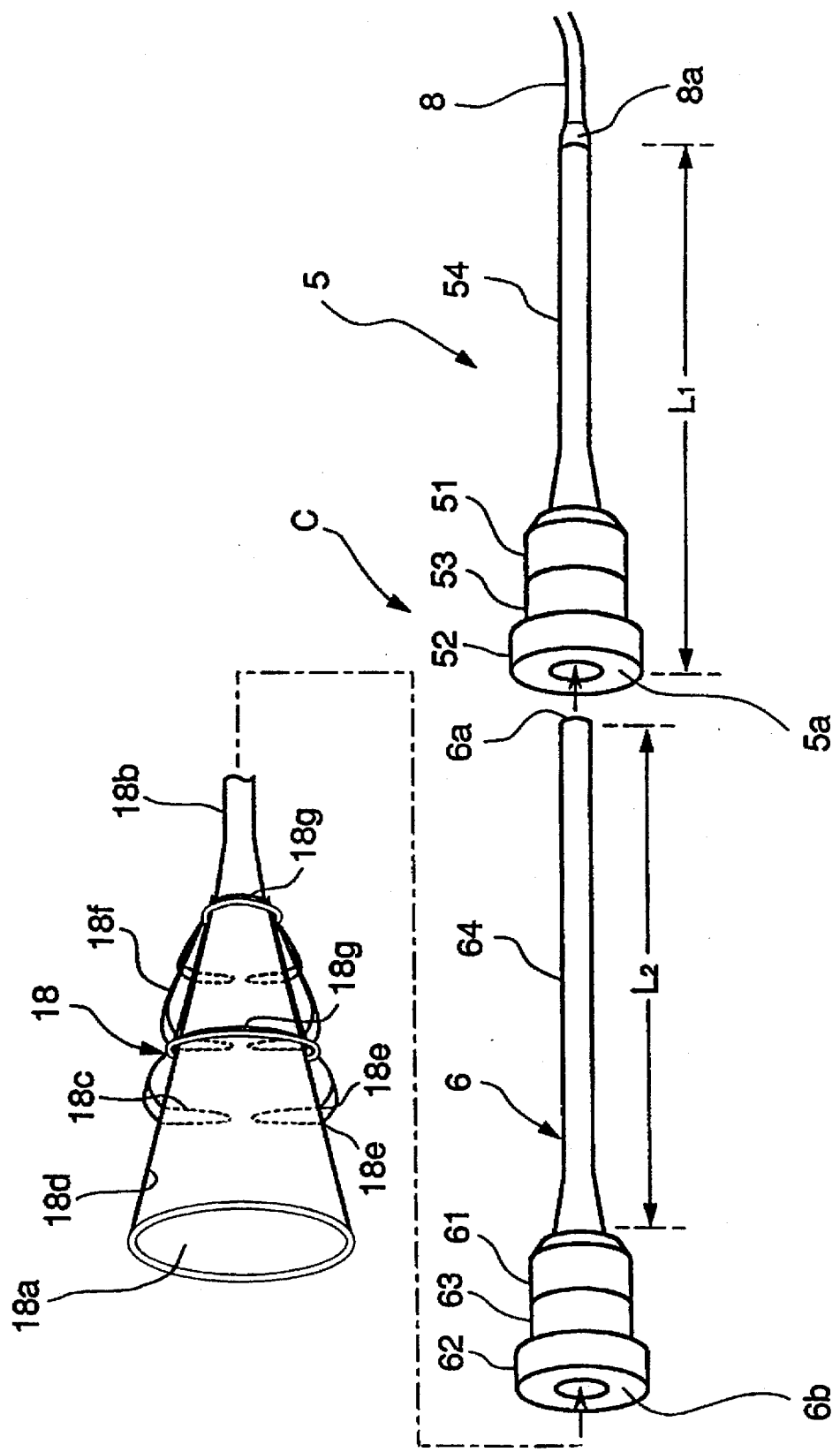
FIG. 4 is a perspective view of a device for introducing the artificial blood vessel, used in the embodiment.
Figure 5:
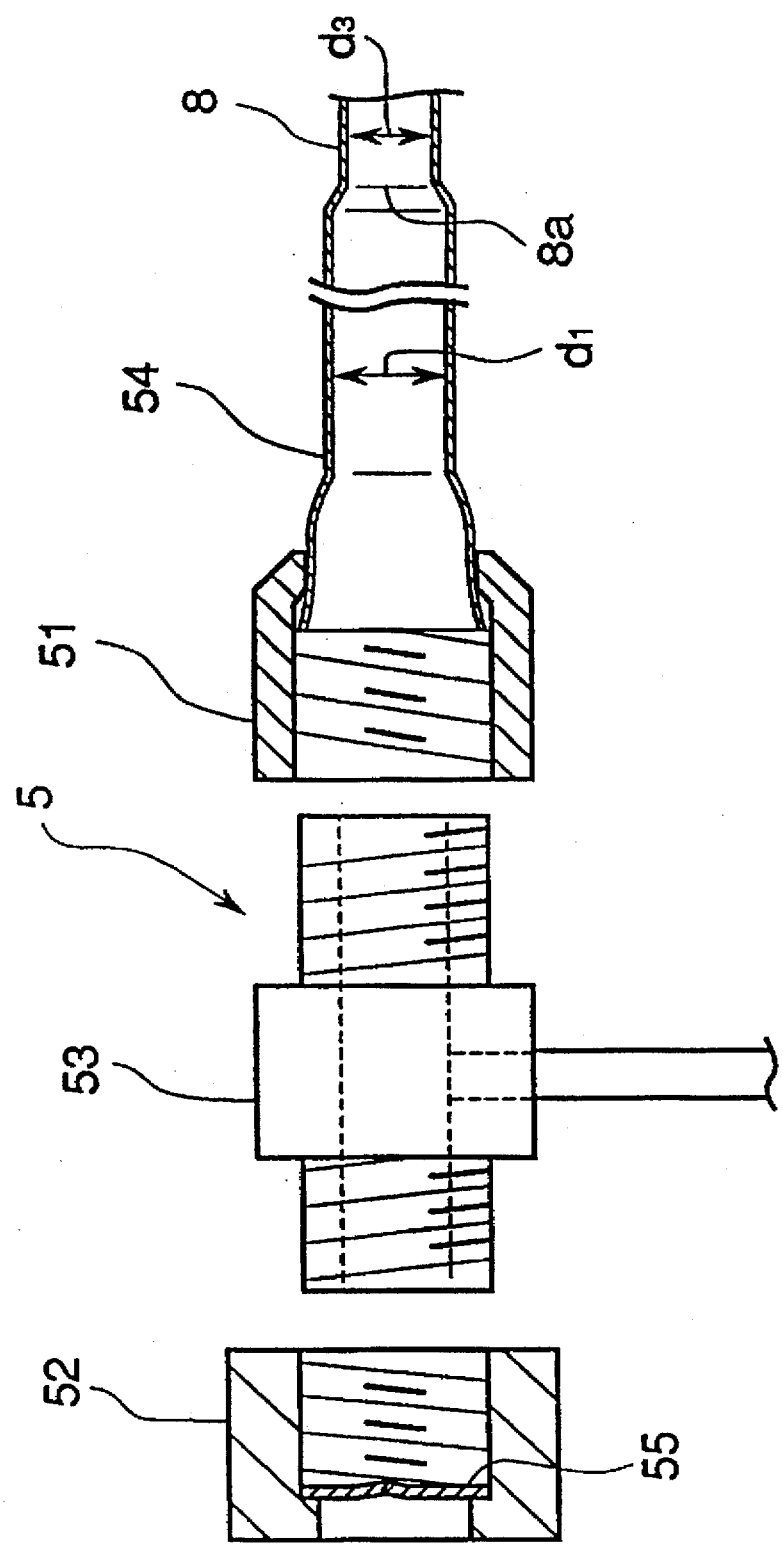
FIG. 5 is an enlarged vertical cross-sectional view of part of the attachment shown in FIG. 4.
Figure 6:
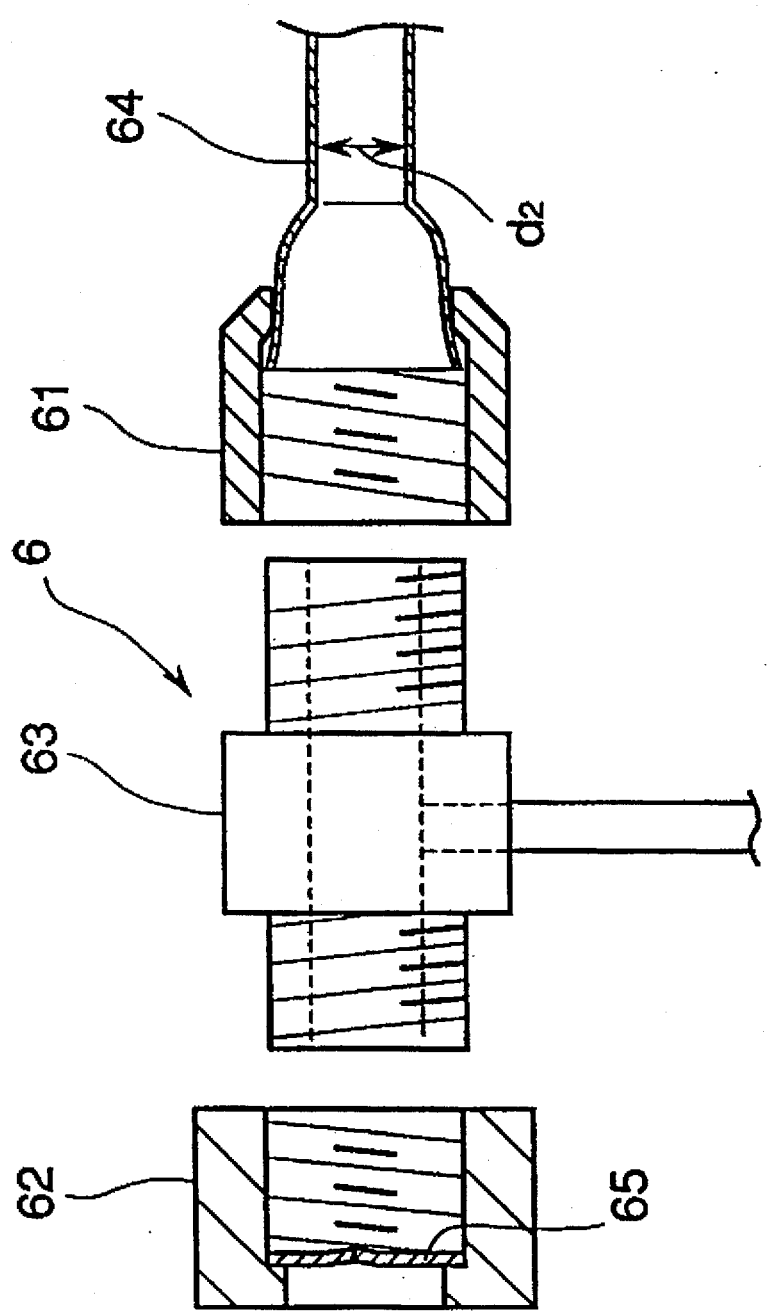
FIG. 6 is an enlarged vertical cross-sectional view of part of the cartridge shown in FIG. 4.

The device C for introducing artificial blood vessels, as shown in FIG. 4, comprises an attachment 5 integrally connected to the catheter 8 through an open end $8a$ thereof, and a cartridge 6 removably attached to the attachment 5. As shown in FIGS. 4 and 5, the attachment 5 comprises a first and a second annular member 51, 52 which are internally threaded to form female screws, a thid annular member 53 which is externally threaded to form male screws at opposite ends, which engage the above-mentioned female screws thereby to connect the first-and the second annular members 51, 52, and a straw member 54 which liquid-tightly joins the interior of the first annular member 51 with that of the open end 8a of the catheter 8. A check valve 55 made of elastic membrane is provided inside the second annular member 52 to close the open end thereof. The cartridge 6, as shown in FIG. 4 and 6, is of generally the same construction as the attachment 5 and comprises first and second annular members 61, 62 which are internally threaded to provide internal female screws, a third annular member 63 which is externally threaded to form male screws at opposite ends, which engage the above-mentioned female screws at opposite ends to connect the first and second annular members 61, 62, and a straw member 64 which projects from the first annular member 61 in the direction of insertion. A check valve 65 made of elastic membrane is provided inside the second annular member 62 to close the open end thereof.

As shown in FIG. 4, the straw member 64 of the cartridge 6 is so constructed that the front end portion 6a thereof is removably fitted into the rear end portion 5a of the attachment 5 which is connected integrally to the open end 8a of the above-mentioned catheter 8. In particular, as shown in FIGS. 4, 5, and 6, the bore diameter $d_1$ of the straw member 54 of the attachment 5 is a little larger than the bore diameter $d_2$ of the straw member 64 of the cartridge 6, and the length $L_2$ of the straw member 64 is approximately equal to the full length $L_1$ of the attachment 5. Similarly the bore diameter $d_2$ of the straw member 64 of the cartridge 6 is approximately equal to the bore diameter $d_3$ of the open end 8a of the catheter 8. When the cartridge 6 is inserted a certain length into the attachment 5, the straw member 64 is inserted into the straw member 54 so that the bore $d_2$ of the straw member 54 is smoothly connected to the bore $d_3$ of the open end 8a of the catheter 8. The above-mentioned check valves 55, 65 are made of elastic membrane, in each of which a normally closed hole, not shown in drawings, is formed.

A funnelled tube 18, as shown in FIG. 4, is provided as a guide tube to help collapse the artificial blood vessel A. The funnelled tube 18 is provided with an inlet opening 18a of an enlarged diameter at the rear end portion, through which the tubular artificial blood vessel A is inserted into the funnelled tube 18. The funnelled tube 18 is gradually reduced in diameter from the inlet opening 18a to end in a tubular connector 18b of a smaller diameter at the front end portion thereof, so that the tube 18 has a tapered inner surface 18d. The funnelled tube 18 is removably connected to the cartridge by inserting the front connector 18b into the rear end portion 6b of the cartridge 6. Elastically transformable projections 18c are provided at regular intervals from the rear end portion to the front along two specific generatrices on the tapered inner surface 18d of the funnelled tube 18. When the artificial blood vessel A travels along the tapered inner surface 18d of the funnelled tube 18, the projections 18c are elastically transformed by the vessel A to exert a resilient counterforce to the artificial blood vessel A thereby to contract vessel A.

In order to form the projections 18c with ease, as shown in FIG. 4, several pairs of holes 18e are formed on the tapered wall 18d of the funnelled tube 18, and a wire 18f is inserted through one of each pair of holes 18e and drawn out through the other of the pair of holes 18e so as to form a looped projection 18c erect on the inner side of the tapered inner surface 18d, with appropriate portions of the wire 18f being tied with a string 18g.

The operations of collapsing the artificial blood vessel A and implanting it into a target portion (an affected part 26) of a blood vessel 9 by means of the device B for transporting artificial blood vessels and the device C for introducing artificial blood vessels of the above-mentioned constructions, will now be described below.

Figure 7:
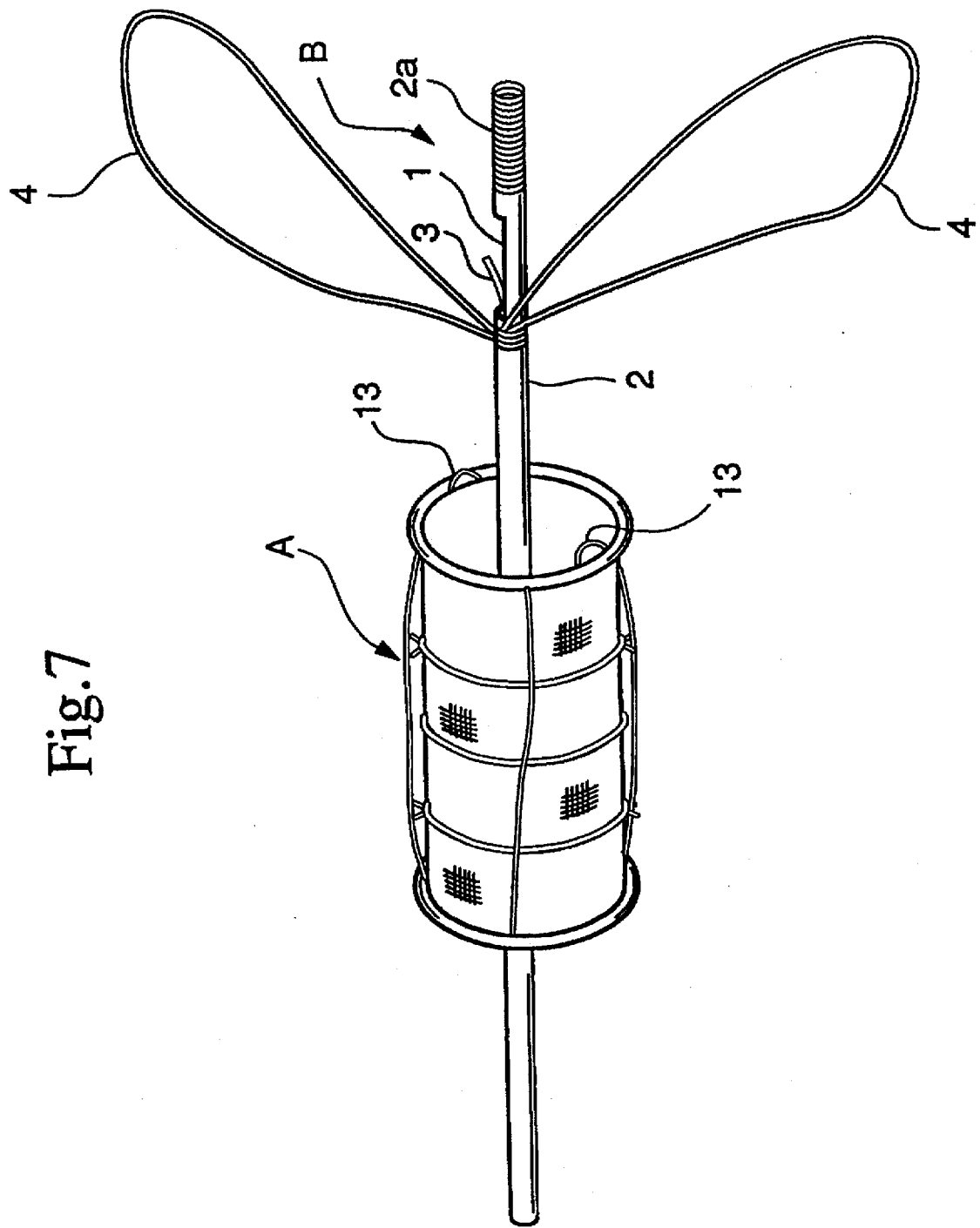
FIG. 7 is a perspective view of the artificial blood vessel through which the device for transporting the artificial blood vessel is loosely inserted.
Figure 8:
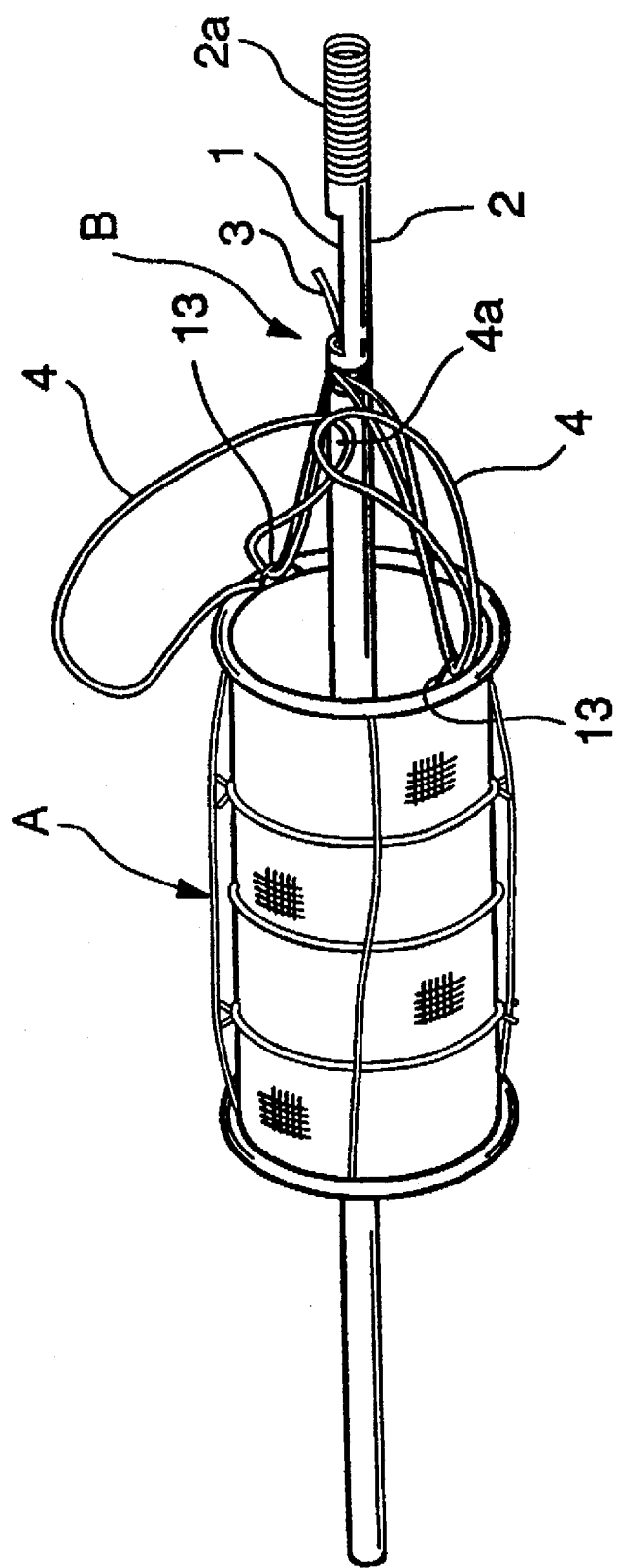
FIG. 8 is a perspective view showing a step to hold the artificial blood vessel by means ok the device for transporting the artificial blood vessel.
Figure 9:
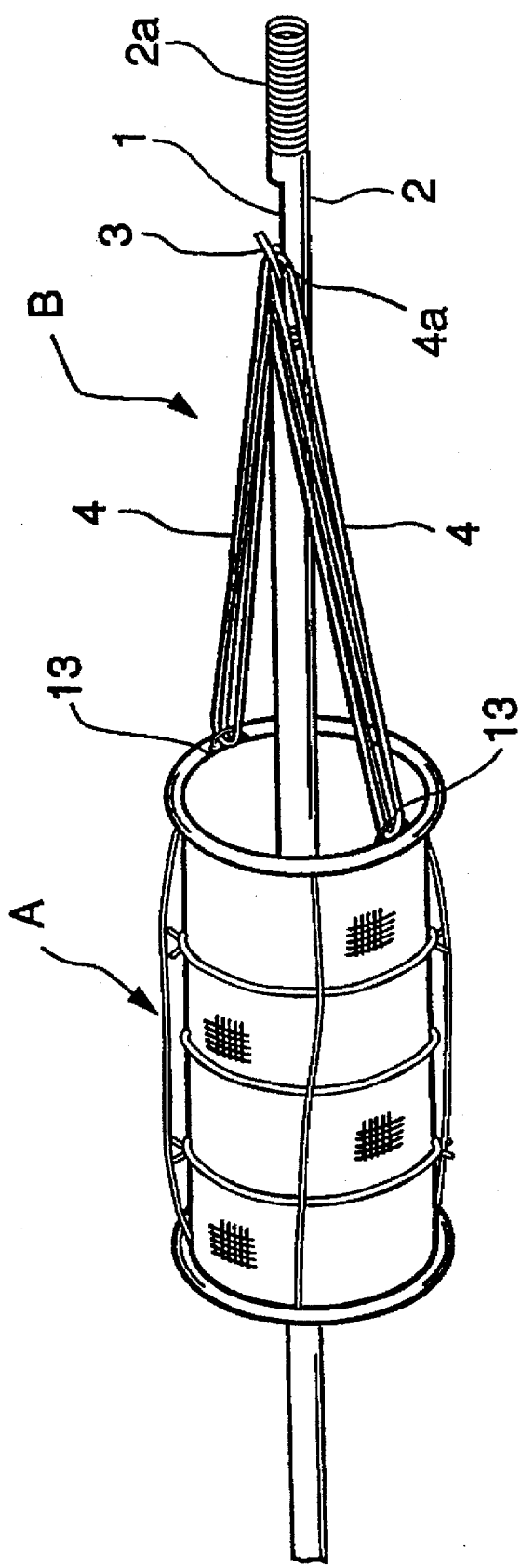
FIG. 9 is a perspective view showing a step to hold the artificial blood vessel by means of the device for transporting the artificial blood vessel.
Figure 10:
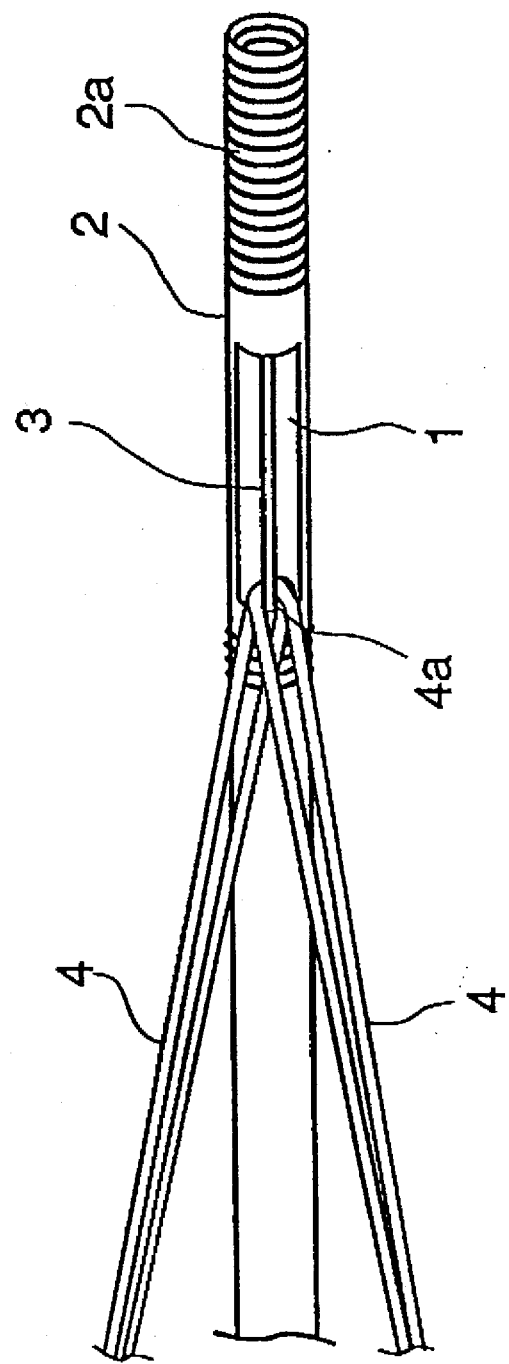
FIG. 10 is an enlarged perspective view showing part of the artificial blood vessel kept by the device for transporting the artificial blood vessel.
Figure 11:
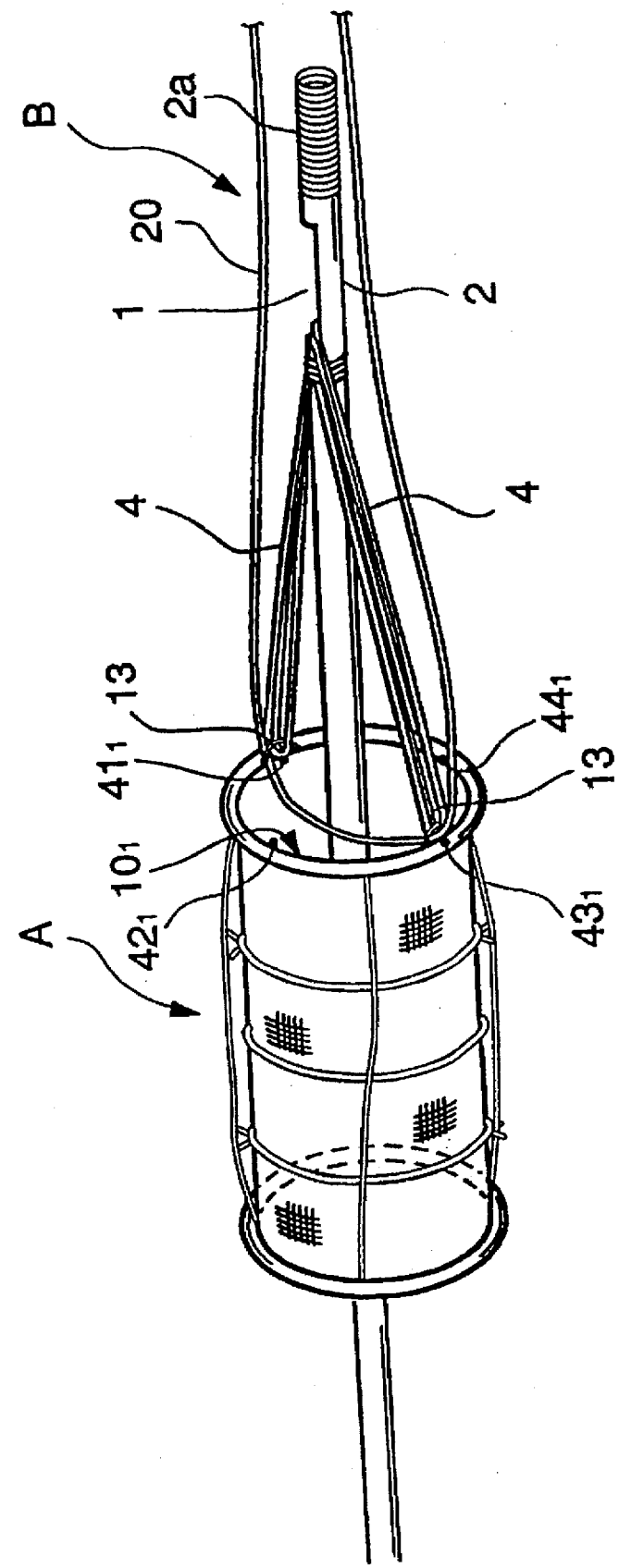
FIG. 11 is a perspective view showing a step to introduce the artificial blood vessel into a catheter.
Figure 12:
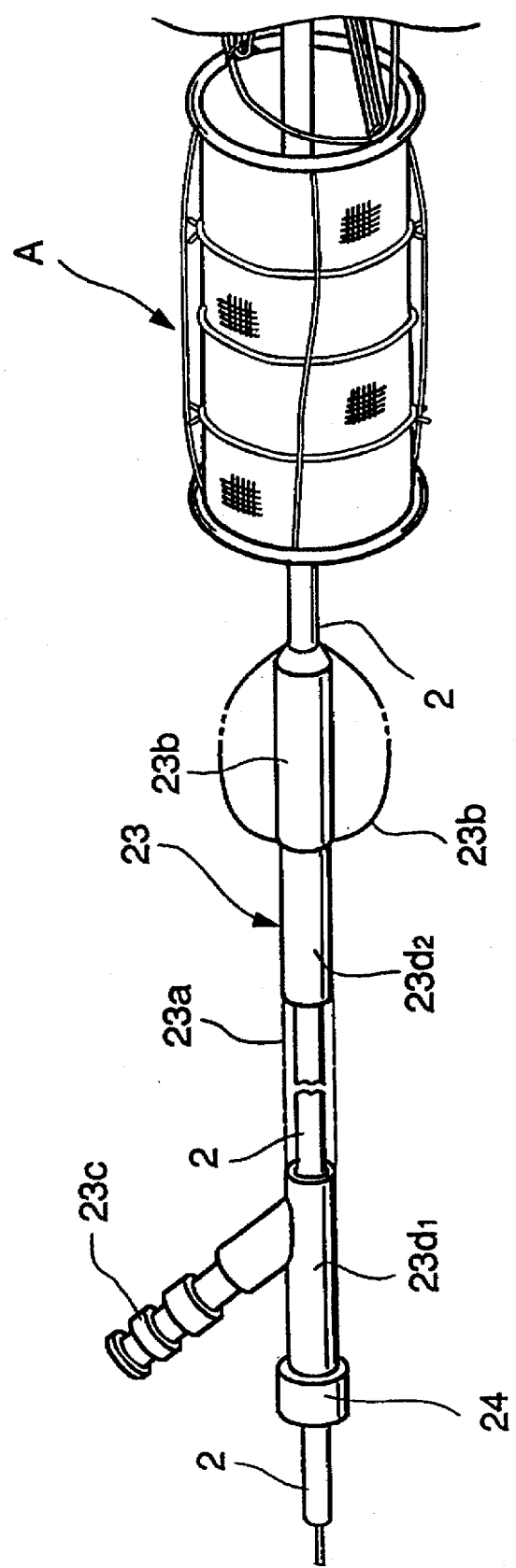
FIG. 12 is a perspective view showing a step to introduce the artificial blood vessel into the catheter.

First, the tube 2 is inserted through the artificial blood vessel A as shown in FIG. 7, and each of a pair of strings 4 is passed through each loop 13 of the artificial blood vessel A as shown in FIG. 8, and the looped portions of the strings 4 overlap as shown at 4a. Next, a wire 3 has its forward end taken out of the side window 1 as shown in FIG. 9, and the overlapped portions of the looped portions 4a are hooked over the wire 3, and then the wire 3 has its forward end inserted again into the tube 2 through the side window 1 so as to hold the artificial blood vessel A on the wire 3 and the tube 2 through the strings 4. Then, the artificial blood vessel A is inserted into the cartridge 6 shown in FIG. 4 through the funnelled tube 18. In particular, the midpoints $42_1$, $44_1$ are aligned with the above-mentioned generatrices of the funnelled tube 18, with a common front pull string 20 being passed through the loops 13 provided at the dividing points $41_1$, $43_1$ on the front end wire ring $10_1$ of the artificial blood vessel A as shown in FIG. 11. A balloon catheter 23, as shown in FIG. 12, may be used, if necessary. The balloon catheter 23 comprises a pipe 23a, a balloon 23b formed on the front end portion of the pipe 23a, and an opening 23c provided in the rear end of the pipe 23a for air to be introduced into or taken out of the above-mentioned balloon 23b through the pipe 23a. The pipe 23a is loosely fitted over the tube 2 of the above-mentioned device B for transporting artificial blood vessels. In other words, the rear end portion of the device B for transporting artificial blood vessels is drawn outside from the rear end of the balloon catheter 23 while the front end portion of the device is passed through the balloon 23b of the balloon catheter 23 and exposed outside, with the portions of the catheter 23 through which the tube 2 is passed being airtightly sealed. The rear end portion of the pipe 23a is removably connected to the tube 2 of the device B for transporting artificial blood vessels by a fixing member 24, and the balloon catheter 23 and the tube 2 of the device B for transporting artificial blood vessels can be moved together as a unit longitudinally when the fixing member 24 is fastened, and the balloon catheter 23 can be moved longitudinally relative to the tube 2 of the device B when the fixing member 24 is loosened. The balloon catheter 23 is so positioned that the front end thereof is spaced about 2 to 3 cm apart from the rear end of the artificial blood vessel A loosely fitted over the tube 2. Then the fixing member 24 on the balloon catheter 23 is fastened to fix the catheter 23 to the tube 2 so that the catheter 23 and the tube 2 can be moved together as a unit.

Figure 13:
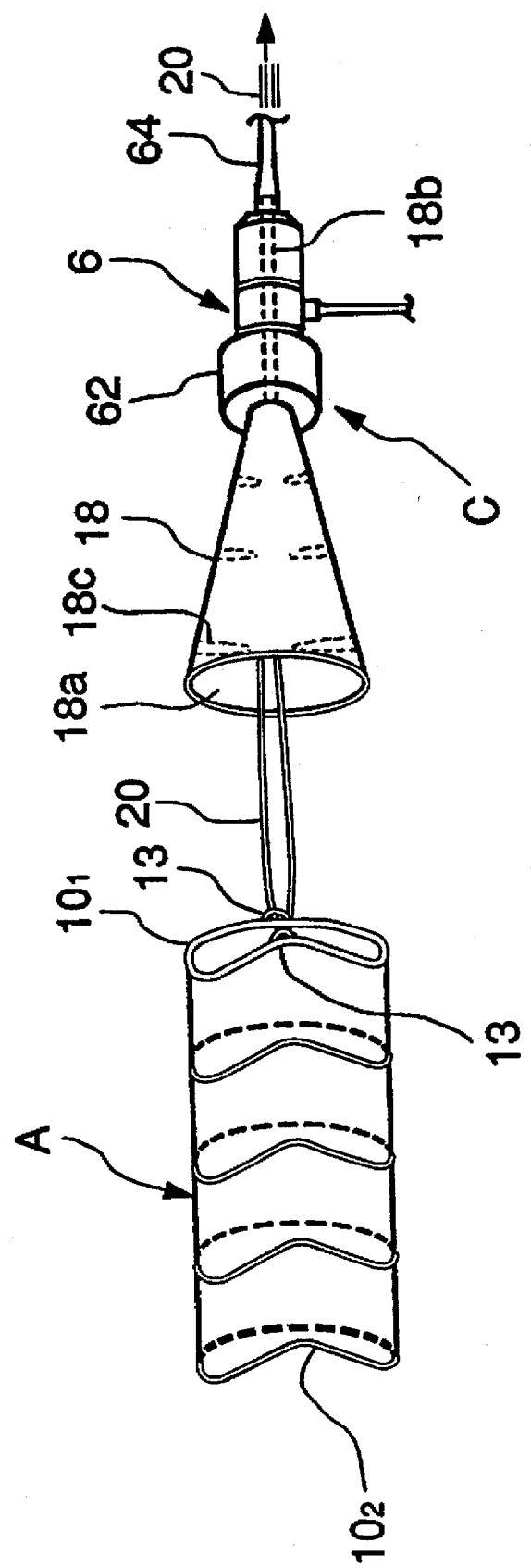
FIG. 13 is a perspective view showing a step to introduce the artificial blood vessel into the catheter by means of the device for introducing the artificial blood vessel.

Before or after the above step, the funnelled tube 18 is attached to a cartridge 6 as shown in FIG. 13. In attaching the funnelled tube 18 to the cartridge 6, the connector 18b of the funnelled tube 18 is inserted into the annular member 62 of the cartridge 6 so that the check valve 65 of elastic membrane provided inside the annular member 62 is pushed open by the connector 18b of the funnelled tube 18, and the connector 18b is inserted a little into the straw 64 of the cartridge 6. The front pull string 20 is inserted into the funnelled tube 18 through the rear end portion 18a thereof and withdrawn forward through the straw 64 at the front end of the cartridge 6, with the tube 2 inserted a certain length into the funnelled tube 18. Under the condition, the front pull string 20 is pulled forward to introduce the artificial blood vessel A into the funnelled tube 18 through the enlarged inlet opening 18a thereof.

Figure 14:
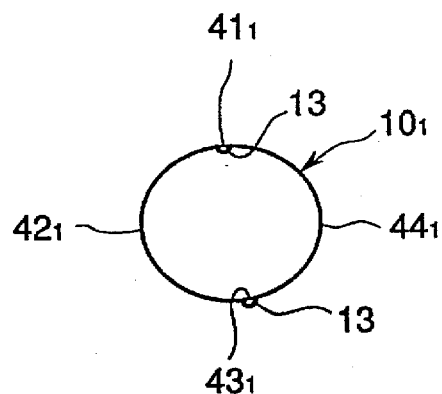
FIG. 14 shows the front end wire ring of the artificial blood vessel being folded.
Figure 15:
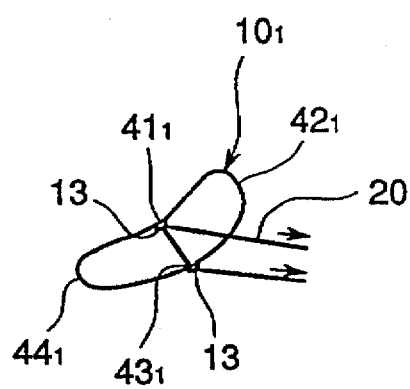
FIG. 15 shows the front end wire ring of the artificial blood vessel being folded.
Figure 16:
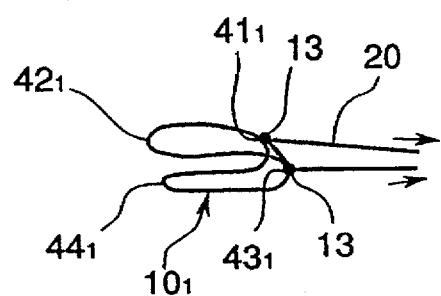
FIG. 16 shows the front end wire ring of the artificial blood vessel being folded.
Figure 17:
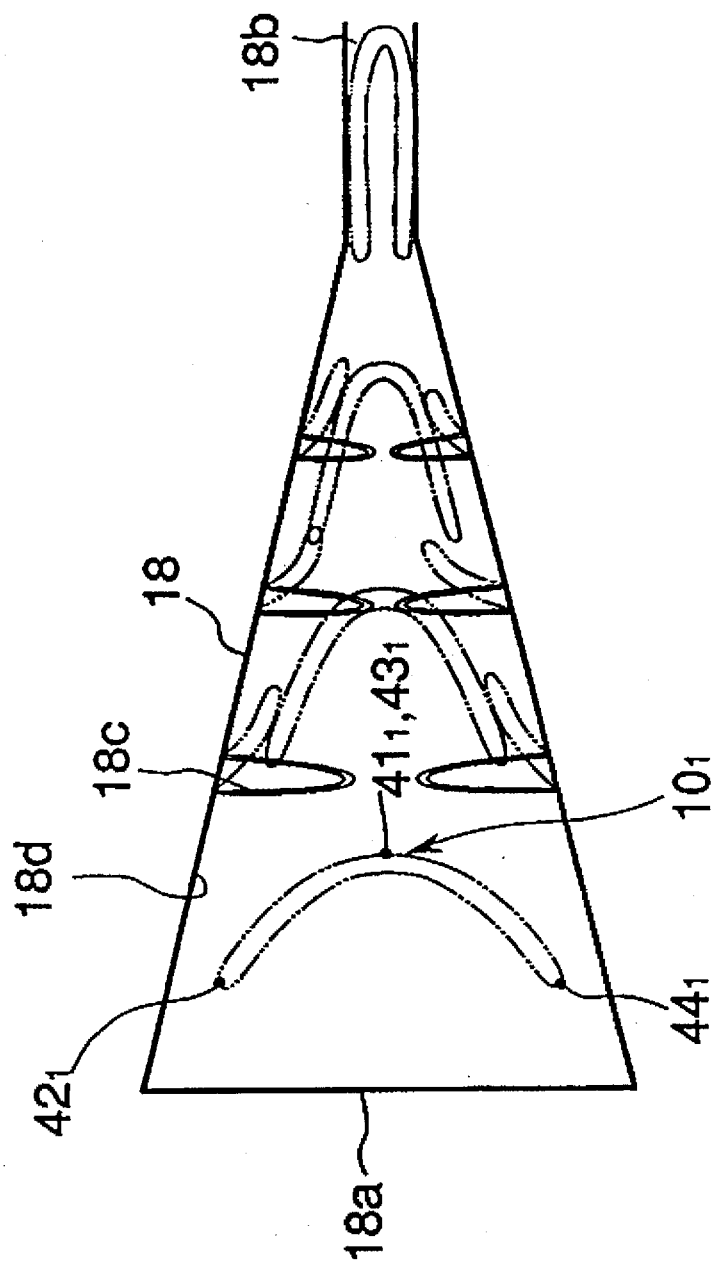
FIG. 17 shows the front end wire ring of the artificial blood vessel being folded in a funnelled tube.
Figure 18:
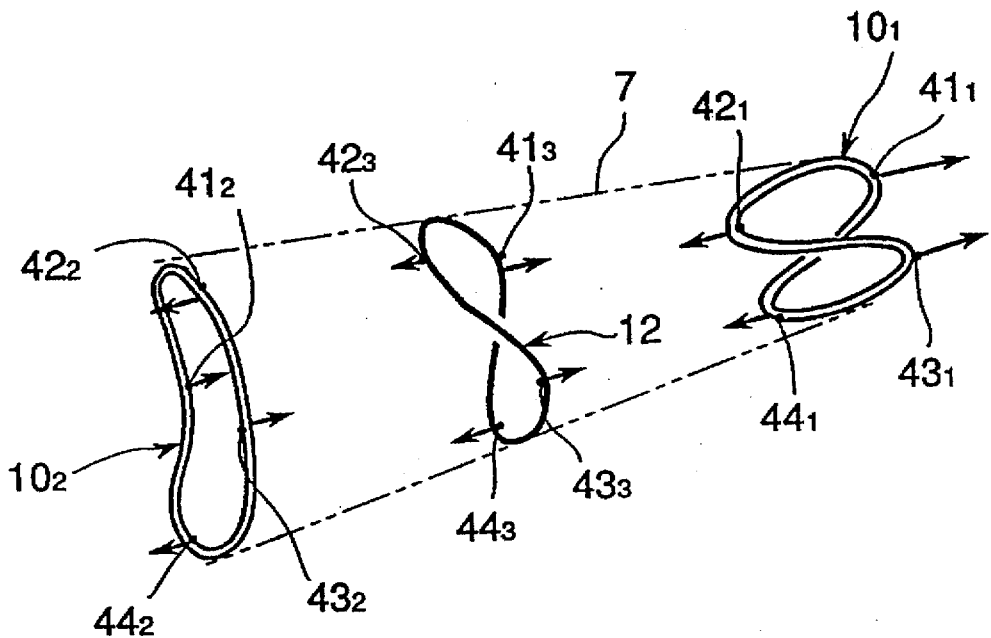
FIG. 18 shows the intermediate wire rings and the rear end wire rings of the artificial blood vessel being folded.
Figure 19:
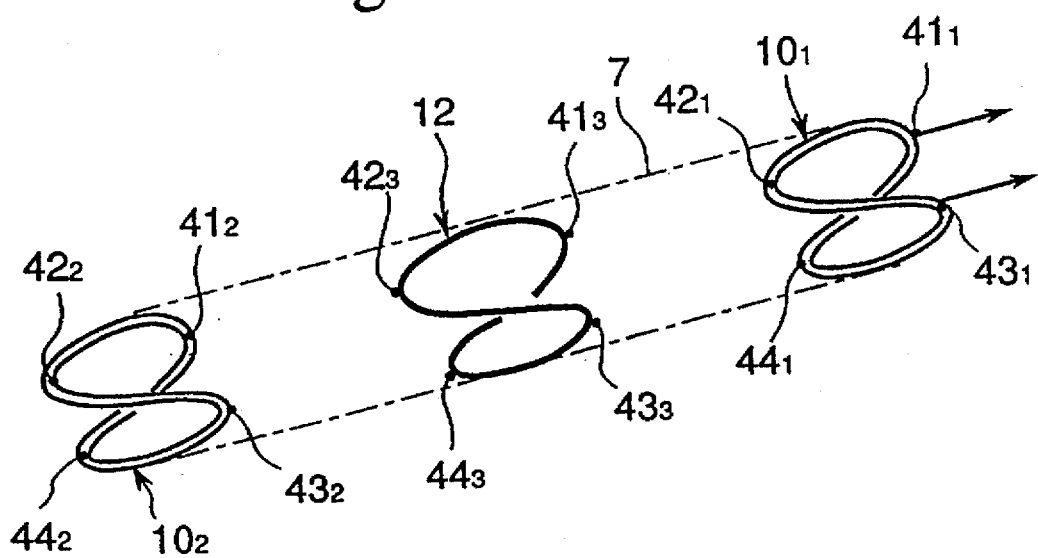
FIG. 19 shows the collapsed artificial blood vessel.

Under the condition, as the front pull string 20 is farther pulled, the dividing points $41_1$, $43_1$ on the front end wire ring $10_1$ of the artificial-blood vessel A are pulled by the front pull string 20, as shown in FIG. 14, and the midpoints $42_1$, $44_1$ are engaged by the projections 18c provided along the generatrices on the tapered surface 18d, so that the front end wire ring $10_1$ is deformed with the dividing points $41_1$, $43_1$ approaching toward each other with the midpoints $42_1$, $44_1$ serving as footholds as shown in FIG. 15. The midpoints $42_1$, $44_1$ are restricted by the projections 18c and left behind the dividing points $41_1$, $43_1$, and urged by the resilient counterforce of the projections 18c to approach each other, thereby to cause the front end wire ring $10_1$ to be folded flat as shown in FIG. 16. In short, the front end wire ring $10_1$ is transformed from the shape shown in FIG. 14 to the shape shown in FIG. 15, and thence to the shape shown in FIG. 16, with the dividing points $41_1$, $43_1$ where the loops 13 are provided forming forwardly directed peaks and the midpoints $42_1$, $44_1$ forming the bottoms of forwardly directed valleys, so that the front end wire ring $10_1$ as a whole takes a regular wavy shape. In short, as shown in FIG. 17, the front end wire ring $10_1$ is passed through the funnelled tube 18 while being farther folded. Since the cover 7 is tensile, as the front pull string 20 is pulled forward, the pulling force is transmitted through the cover 7 to the points $41_3$, $43_3$ on the intermediate rings 12 corresponding to the dividing points and the points $41_2$, $43_2$ on the rear end wire ring $10_2$ corresponding to the dividing points, as shown in FIG. 18. The points $42_3$, $44_3$ on the intermediate rings 12 corresponding to the midpoints and the points $42_2$, $44_2$ on the rear end wire ring $10_2$ corresponding to the midpoints are restrained by the projections 18c when they move along the generatrices on the tapered surface 18d, with the points $41_3$, $43_3$, $41_2$, $43_2$ corresponding to the dividing points forming forwardly directed peaks and the points $42_3$, $44_3$, $42_2$, $44_2$ corresponding to the midpoints forming the bottoms of forwardly directed valleys, as shown in FIG. 19, so that the intermediate wire rings 12 and the rear end wire ring $10_2$ are also folded to take a wavy shape having the same phase as that of the front end wire ring $10_1$. As the rings $10_1$ and $10_2$ are folded, the braid members 10a circumferentially arranged about the end wire rings $10_1$, $10_2$ are also folded to take a wavy shape. As the artificial blood vessel A is collapsed, the thorns $12a_1$ are pushed down to extend rearward or forward because of the above-mentioned construction.

Figure 20:
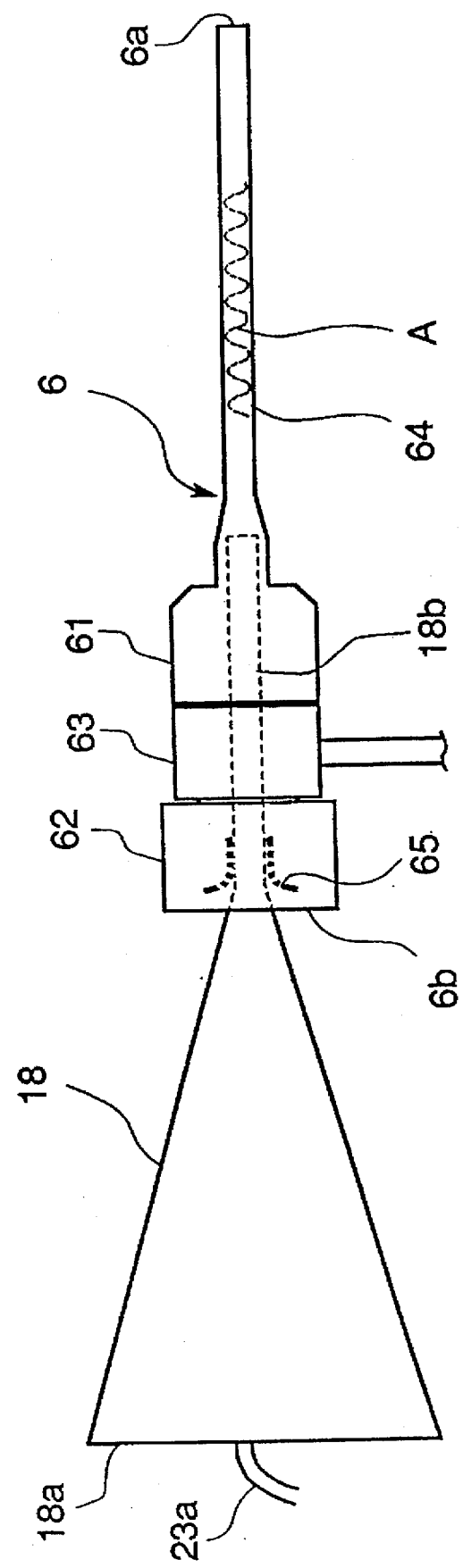
FIG. 20 shows the artificial blood vessel being inserted into the cartridge.
Figure 21:
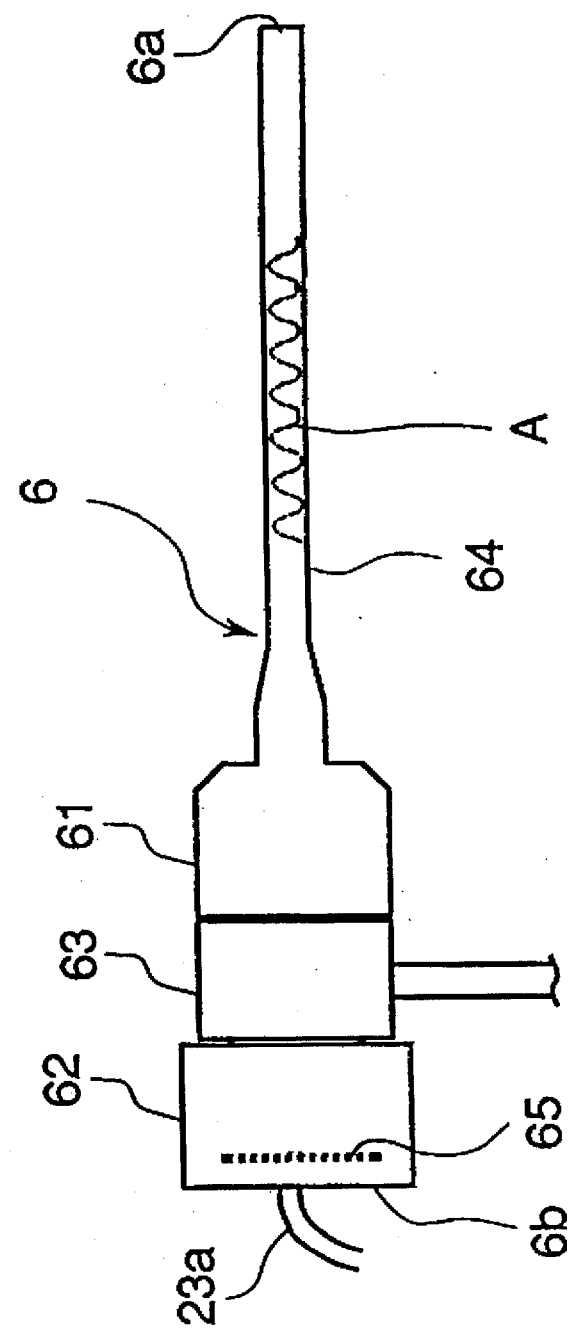
FIG. 21 shows the artificial blood vessel inserted into the cartridge.

Thus, the artificial blood vessel A inserted into the connector 18b is introduced into the straw 64 of the cartridge 6, as shown in FIG. 20, by pulling the front pull string 20 farther forwardly. Under the condition, the front pull string 20 is untied and pulled at its end so as to be withdrawn from the loops 13, and the funnelled tube 18 is withdrawn from the cartridge 6 through the rear end portion 6b thereof. Consequently, the artificial blood vessel A is contained in the straw 64 of the cartridge 6, as shown in FIG. 21, and only the pipe 23a of the balloon catheter 23 through which the tube 2 is passed is exposed outside through the rear end portion 6b of the cartridge 6 with the check valve 65 opened a little.

Figure 22:
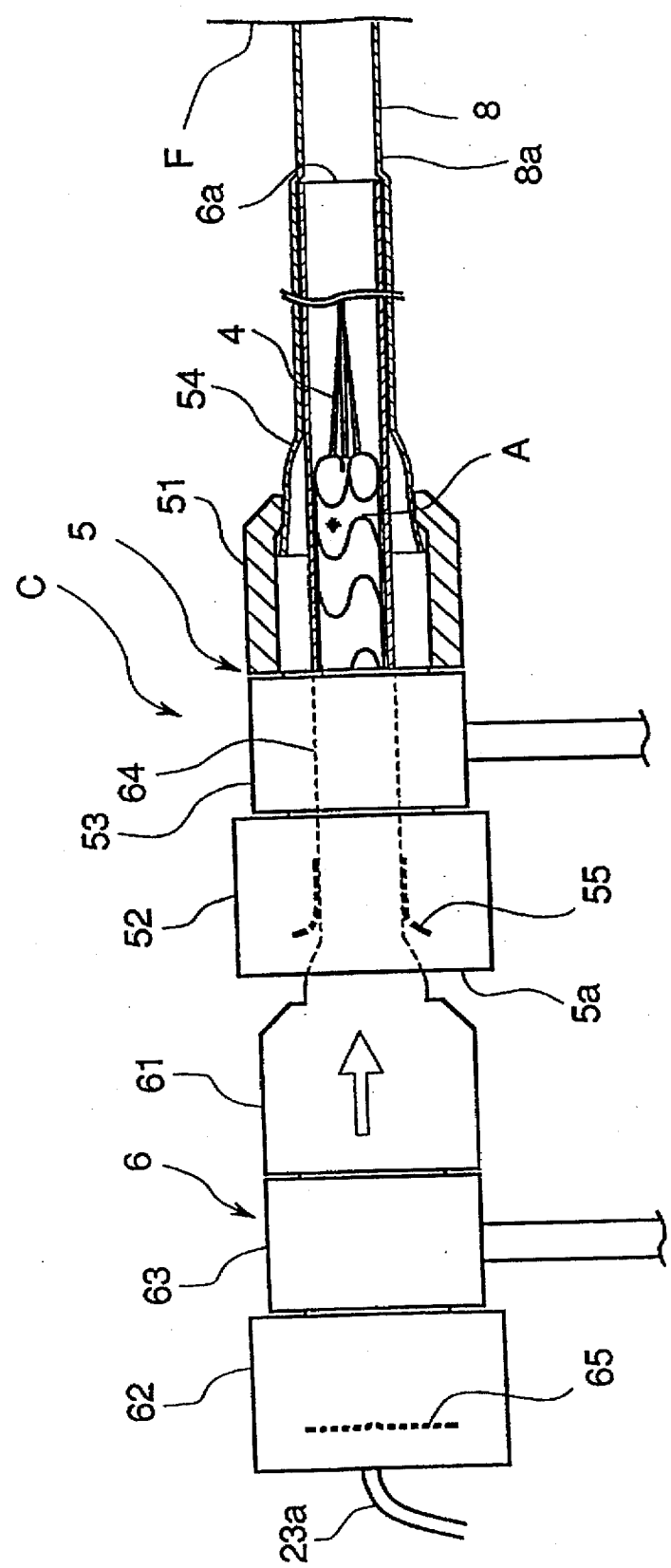
FIG. 22 shows the artificial blood vessel transported from the cartridge to the attachment.
Figure 23:
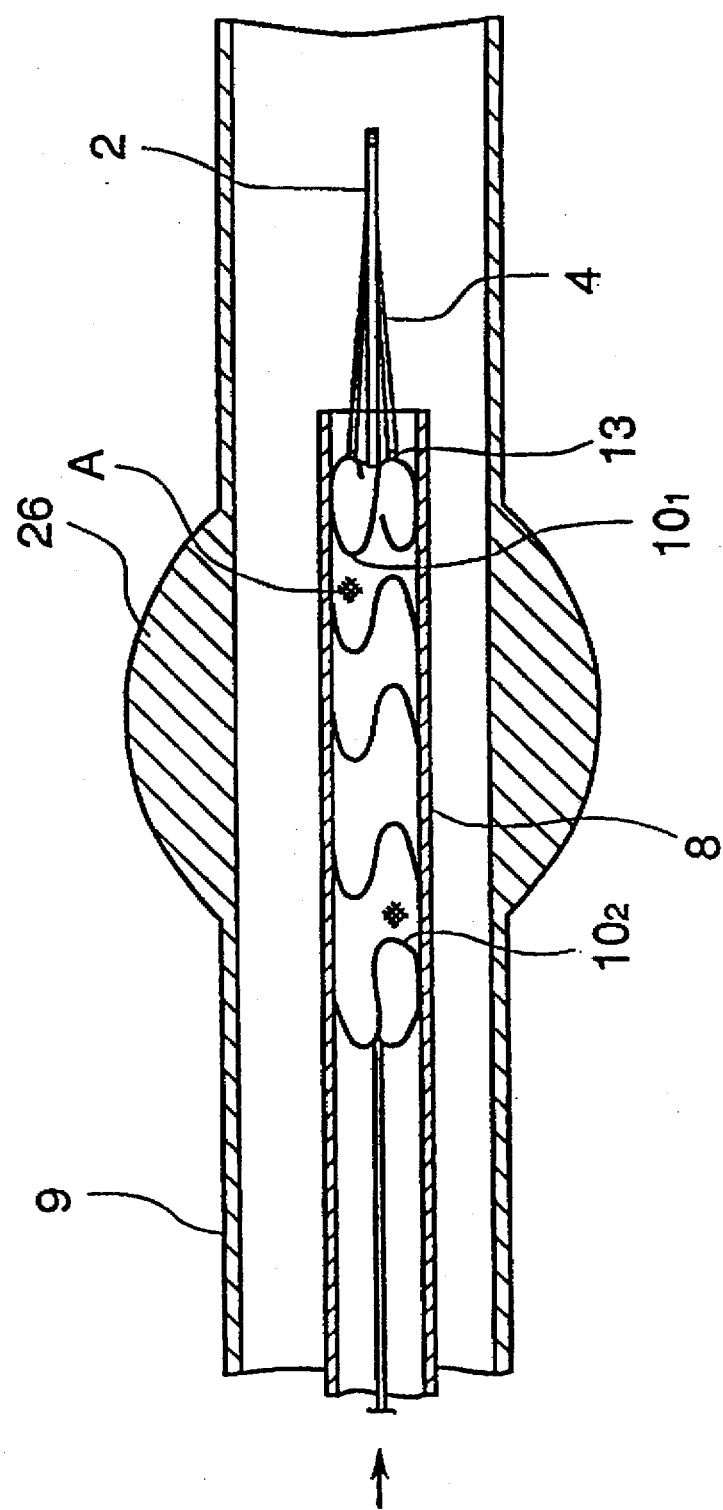
FIG. 23 is a cross-sectional view showing the artificial blood vessel transported to the affected portion.
Figure 24:
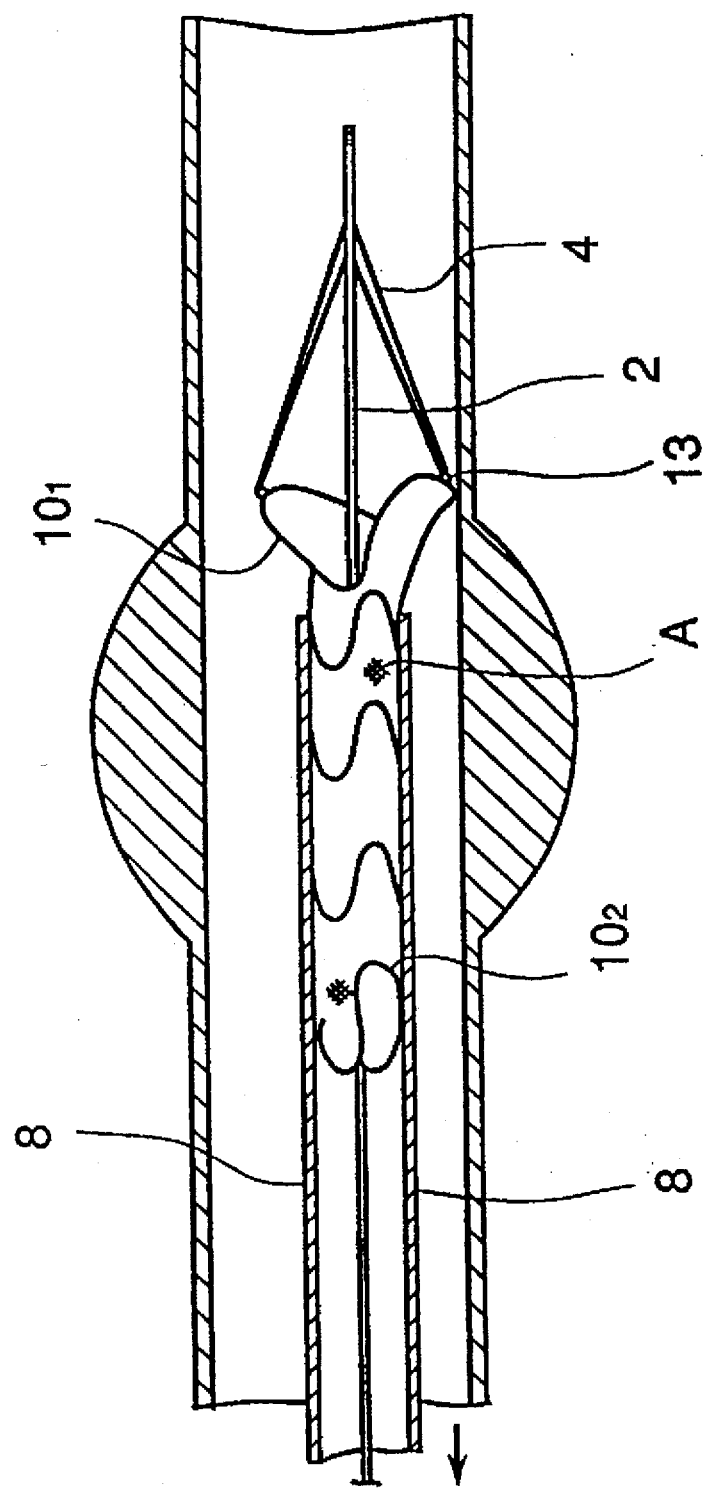
FIG. 24 shows a step to release the artificial blood vessel at an affected part in a blood vessel.
Figure 25:
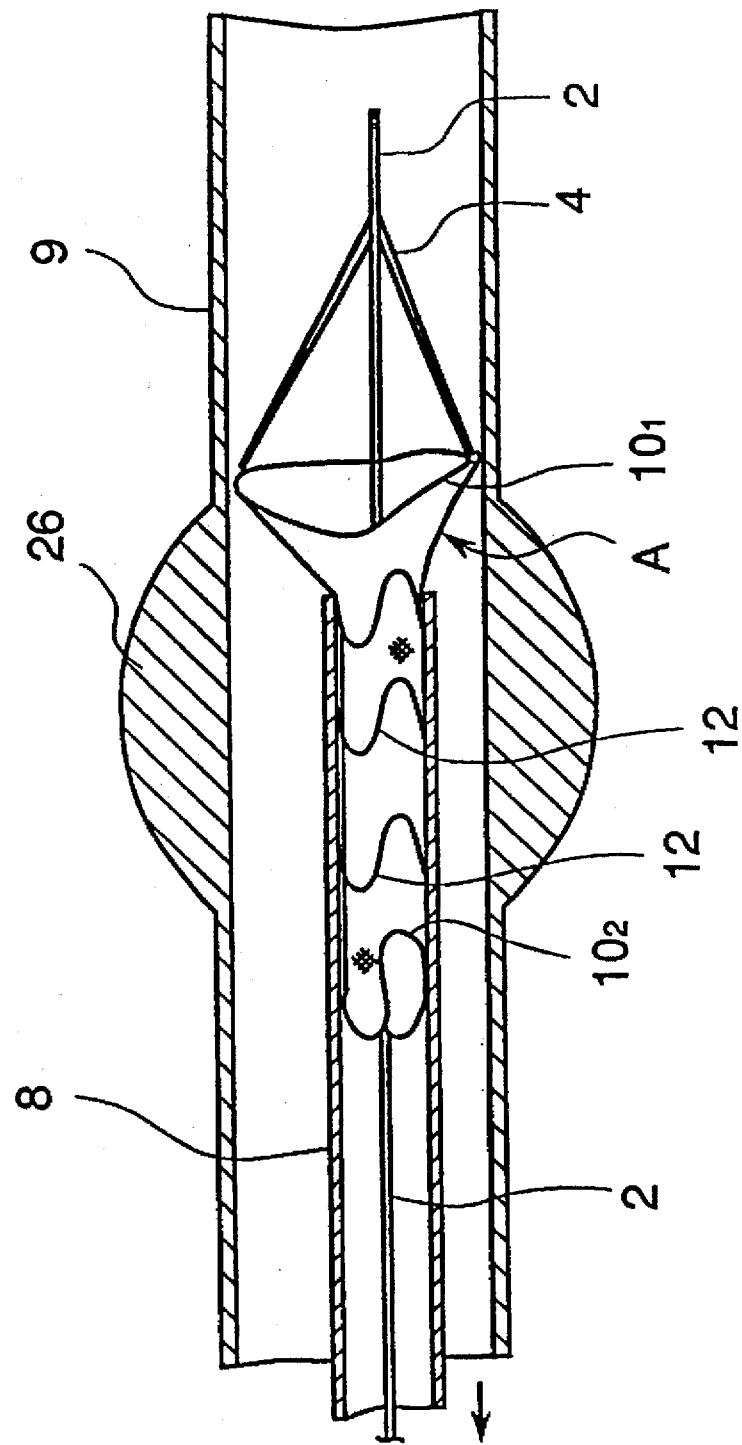
FIG. 25 shows a step to release the artificial blood vessel at the affected part in the blood vessel.
Figure 26:
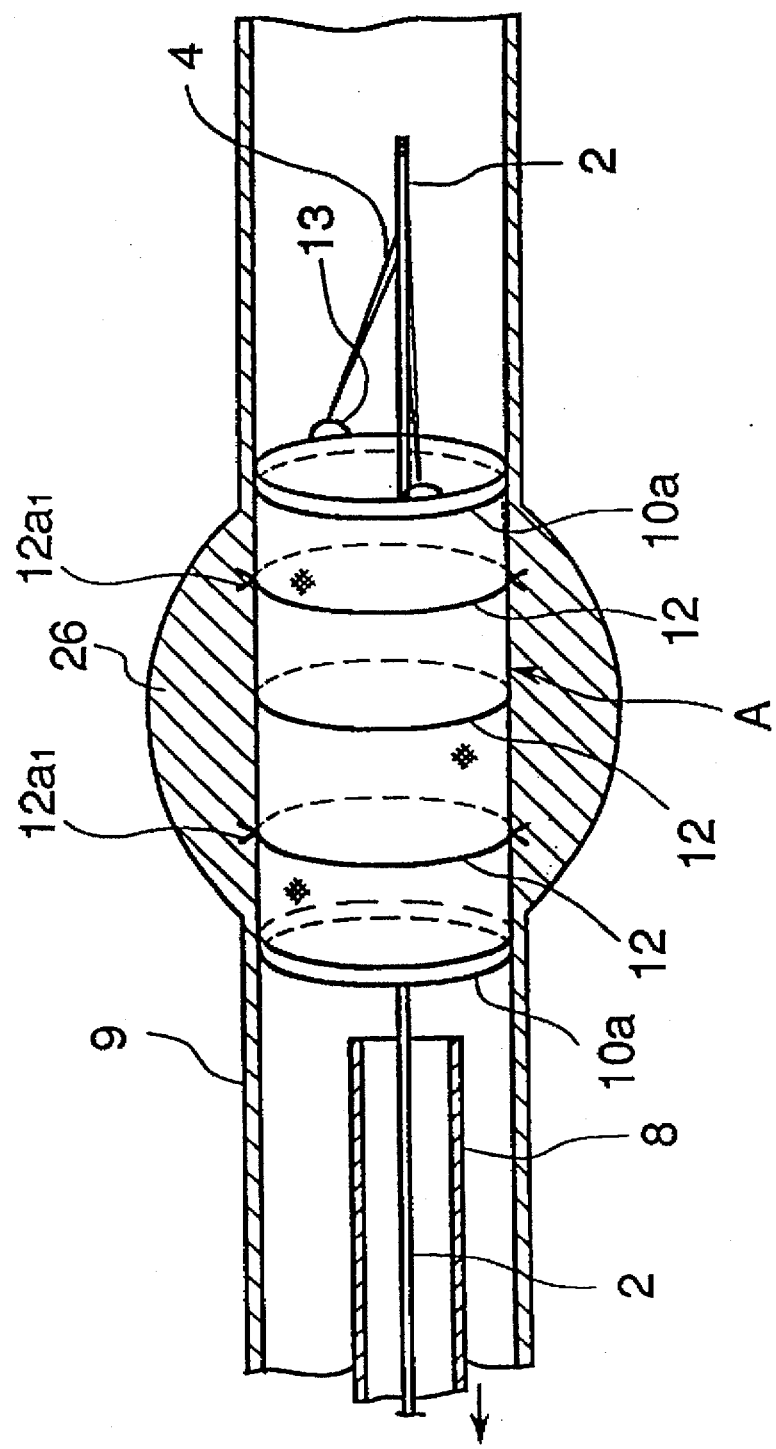
FIG. 26 is a cross-sectional view showing the artificial blood vessel released at the affected portion in the blood vessel.
Figure 27:
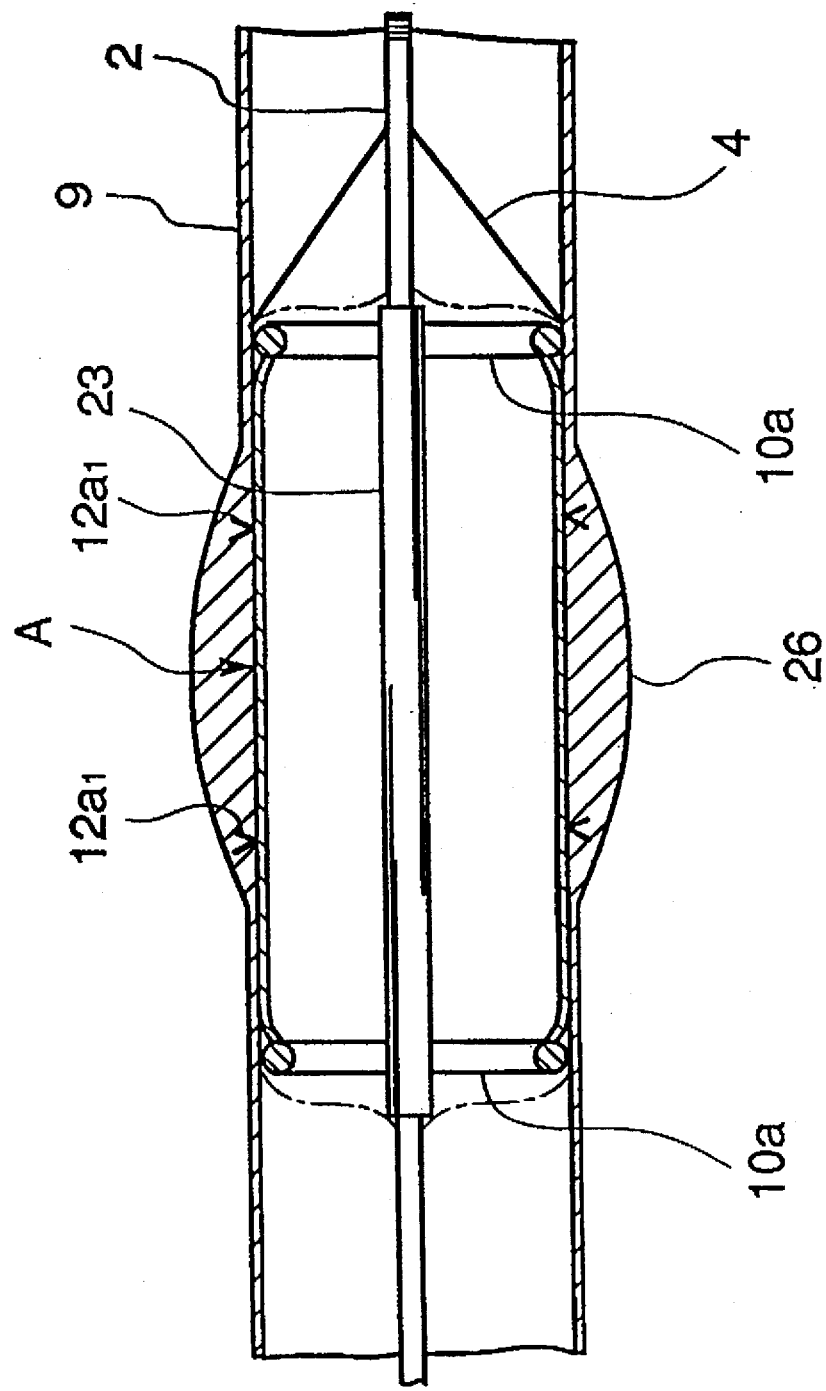
FIG. 27 shows a step to expand the artificial blood vessel by means of a balloon catheter.

On the other hand, the catheter 8 has been previously inserted through, for example, the coxal artery adjacent the groin F into the blood vessel 9 as far as the front end of the catheter 8 has been positioned a little beyond the affected portion 26 such as an aneurysm of the aorta. The attachment 5 connected to the open end 8a of the catheter 8 is, as shown in FIG. 22, exposed outside the body. Next, the cartridge 6 into which the artificial blood vessel A has been inserted is pushed into the attachment 5 through the rear end portion 5a thereof with the check valve 5 opened, and the straw 64 of the cartridge 6 is positioned so that the front end 6a thereof is smoothly connected to the inner surface of the open end 8a of the catheter 8. Under the condition, the pipe 23a of the balloon catheter 23 is gripped and the balloon catheter 23 is pushed so as to be inserted gradually deeply into the catheter 8. As the tube 2 is connected to the balloon catheter 23 through the fixing member 24 and the artificial blood vessel A is held by the tube 2, movement of the balloon catheter 23 causes the artificial blood vessel A to be transported gradually to the deep position in the body. The balloon catheter 23 is pushed until the front end of the tube 2 is positioned at the front end of the catheter 8, as shown in FIG. 23. At this time the artificial blood vessel A is positioned at the affected portion 26 as the target position. Then, as the catheter 8 is withdrawn as shown in FIG. 24, with the balloon catheter 23 and the tube 2 into which the wire 3 is inserted left at the objective position, the collapsed artificial blood vessel A in the catheter 8 is released at the affected portion 26 in the blood vessel 9 while expanding gradually from the front end as shown in FIGS. 24, 25 and 26. The released artificial blood vessel A is restored to its original tubular shape and urged against the inner wall of the blood vessel 9. Then the fixing member 24 shown in FIG. 12 is loosened to disconnect the balloon catheter 23 from the tube 2, and the balloon catheter 23 is advanced along the tube 2 into the artificial blood vessel A with the tube 2 kept at the objective position as far as the front end of the balloon catheter 23 reaches the front end of the artificial blood vessel A as shown in FIG. 27, whereupon the balloon 23b is inflated by introducing air through the opening 23c as shown by dash-and-dot lines in FIG. 27 thereby to restore the artificial blood vessel A completely to its original shape and securely fix it onto the inner wall of the blood vessel. At this time the thorns stick into the inner wall of the blood vessel 9 and are embedded therein. After the artificial blood vessel A has been thus fixed, the balloon 23b of the balloon catheter 23 is deflated by drawing air through the opening 23c and the balloon catheter 23 is pulled out from the artificial blood vessel A by pulling the pipe 23a rearwardly. Then it is confirmed that the artificial blood vessel A has been fixed onto the inner wall of the blood vessel 9, and then the wire 3 is pulled out of the tube 2. As the front end of the wire 3 passes the rear edge of the side window 1 of the tube 2 as shown in FIG. 8, the loop portion 4a of the string 4 that has been caught by the wire 3 at the side window 1 is released from the wire 3. Under the condition, when the tube 2 is pulled out, the string 4 slips out of the loops 13 of the artificial blood vessel A. The balloon catheter 23 and the tube 2 are then connected again by the fastener 24 and pulled out of the human body with only the artificial blood vessel A left at the desired position in the blood vessel 9.

As mentioned above, in accordance with the invention, the artificial blood vessel A is implanted into the affected portion 26, and restored to its original shape thereby to effectively prevent Occlusion of the affected portion 26 in the blood vessel 9. With the above-mentioned collapsing method, the artificial blood vessel A can be collapsed with ease and accuracy. It is difficult to fold the front end wire ring $10_1$ into such a small shape that can be contained in a catheter 8 merely by applying non-directional external forces thereto. However, the dividing points $41_1$, $43_1$ which equally divide the circumference of the front wire ring $10_1$ are pulled forward and the midpoints $42_1$, $44_1$ between the dividing points $41_1$, $43_1$ are restrained from moving forward following the dividing points $41_1$, $43_1$ by a tapered surface $18d$, so that the dividing points $41_1$, $43_1$ form forwardly directed peaks and the midpoints $42_1$, $44_1$ form the bottoms of forwardly directed valleys with the midpoints $42_1$, $44_1$ serving as footholds, so that the front end wire ring. $10_1$ as a whole takes a regular wavy shape. After the front end wire ring $10_1$ has been folded, as the dividing points $41_1$, $43_1$ provided on the front end wire ring $10_1$ are farther pulled forward by the front pull string 20, the pulling force is transmitted to the points $41_3$, $43_3$ on the intermediate rings 12 corresponding to the dividing points and the points $41_2$, $43_2$ on the rear end wire ring $10_2$ corresponding to the dividing points through the tensile cover 7, and at the same time the points $42_3$, $44_3$ on the intermediate rings 12 corresponding to the midpoints and the points $42_2$, $44_2$ on the rear end wire ring $10_2$ corresponding to the midpoints are restrained by the tapered surface $18d$, so that the intermediate wire rings 12 and the rear end wire ring $10_2$ are also folded to take a wavy shape having the same phase as that of the front end wire ring $10_1$, thereby to enable the artificial blood vessel A to be collapsed into a small size with ease.

What should especially be referred to is that the method of collapsing the appliance to be implanted in accordance with the invention is characterized by that the end wire rings $10_1$, $10_2$ provided at the opposite ends of the artificial blood vessel A are connected by only a tubular cover 7 which is made of a flexible and tensile sheet; and that the front end wire ring $10_1$ is pulled forward by means of the device B for transporting artificial blood vessels. The conventional method, in which the appliance to be implanted is pushed at the rear end-so as to be inserted into a human organ, requires a relatively strong frame mainly of connecting wire rings in order to transmit the force applied to the rear end portion of the appliance to the forward portion thereof. However, the invention is based on the idea of pulling the front end wire ring $10_1$ forward, thereby to make insertion of the appliance easy even though no frame is provided. In addition, the cover 7 is transformed into any desired shape as the wire rings $10_1$, 12, $10_2$ are folded, thereby to avoid the mutual interference of the cover 7 and the wire rings $10_1$, 12, $10_2$ which would otherwise occur if frames are provided. Therefore, the method of collapsing the appliance in accordance with this invention makes it possible to collapse the whole artificial blood vessel A into a small size with ease by folding each of the wire rings $10_1$, 12, $10_2$, into a wavy shape.

In this embodiment, in order to collapse the appliance, the loops 13 are formed at the dividing points $41_1$, $43_1$ of the front end wire ring $10_1$ and the front pull string 20 is passed through the loops 13 and pulled forward, thereby to make the operation of collapsing the appliance very easy. In particular, the pulling force can effectively be transformed to a collapsing force because the dividing points $41_1$, $43_1$ are gathered to approach each other by pulling the common front pull string 20 passed through the pair of loops 13, 13.

In this embodiment, the funnelled tube 18 whose inner surface is gradually reduced in diameter toward the front end thereof is used to collapse the artificial blood vessel A. As the artificial blood vessel A is inserted into the funnelled tube 18 deeper, the dividing points $41_1$, $43_1$ and the midpoints $42_1$, $44_1$ are gathered to approach each other, thereby to enable the artificial blood vessel A as a whole to be collapsed into a small size. In this embodiment, as resiliently deformable projections $18c$ are formed on the tapered inner surface $18d$ of the funnelled tube 18 so as to engage with the midpoints $42_1$, $44_1$, the midpoints $42_1$, $44_1$ are pushed to approach each other by the counterforce of the projections $13c$. A space is formed between the front end wire ring $10_1$ and the funnelled tube 18 due to the projections $18c$, thereby effectively to prevent the artificial blood vessel A from being securely caught in the funnelled tube 18 due to the sliding resistance which would otherwise be increased if the front end wire ring $10_1$ were in tight contact with the funnelled tube 18. The same is true with the intermediate wire rings 12 and the rear end wire ring $10_2$.

In this embodiment, the flexible braid members $10a$ are circumferentially arranged on the end wire rings $10_1$, $10_2$ so as to prevent particularly the front end wire ring $10_1$ from being damaged to cause the artificial blood vessel A to lose its function. In particular, if the front end wire ring $10_1$ is bent beyond its elastic limit, not only it becomes difficult for the ring to be restored to its original annular shape but also it becomes impossible to move the ring in the catheter 8 because the bent portion is caught in the catheter 8. However, as the braid members $10a$ are provided, they diffuse the tension which would otherwise be locally applied to the dividing points $41_1$, $43_1$ when the dividing points $41_1$, $43_1$ are strongly pulled, thereby to prevent the dividing points from being bent beyond the elastic limit of the ring $10_1$. Consequently, the braid members $10a$ prevent plastic deformation of the front end wire ring $10_1$, provide the ring with a proper capability of restoring to the annular shape and of traveling smoothly in a catheter, and enable the front end wire ring $10_1$ to be folded into a regular wavy form.

The artificial blood vessel A constructed without a frame as mentioned above properly functions for the intended purpose. The artificial blood vessel A in accordance with the invention is so constructed that the cover 7 itself is made of a tensile material and is held by the intermediate wire rings 12 at appropriate points thereof, and that when the whole artificial blood vessel A is released from the state of being collapsed and each of the wire rings $10_1$, $10_2$, 12 is resiliently restored to the annular shape, the cover 7 is restored to the original proper tubular shape by the wire rings $10_1$, $10_2$, 12. The conventional appliance having a frame, if put in a bent portion of a human organ, is likely to be deformed flatly because of mutual interference of the component parts. However, the artificial blood vessel A having no frame in this embodiment can be transformed into any desired shape so as to conform to different shapes of human organs.

In this case, as the cover 7 is of a sheet woven with warps and wefts, and the warps are made of mono-filament of polyester (about 15 denier), whose stiffness helps keep the shape of the cover 7, and the wefts are of multi-filament of polyester (about 50 denier), whose closeness gives the sheet waterproofness, the whole cover 7 is flexible, resistive to axial tension, keeps its tubular shape by itself, and can prevent leakage of blood.

As the sheet of the cover 7 is in the form of bellows, the whole artificial blood vessel A is easily bendable so that the condition of the artificial blood vessel A implanted into a human organ is improved. As the restraining strings 14 bridge the end wire rings $10_1$, $10_2$, the bellows can be prevented from stretching beyond the limit to become flat.

In this embodiment, as the flexible braid members $10a$ are circumferentially arranged on the end wire rings $10_1$, $10_2$ of the artificial blood vessel A, the inner wall of a human organ can be prevented from being damaged by direct contact with the end wire rings $10_1$, $10_2$ in addition to the advantage that the front end wire ring $10_1$ can be prevented from being plastically deformed when folded into a small size as mentioned above. The braid members 10a also help seal both ends of the implanted artificial blood vessel A tightly to the inner wall of a human body, thereby to effectively prevent leakage of blood through the ends of the artificial blood vessel A when implanted.

As the thorns $12a_1$ project from the intermediate wire rings 12, they stick into the inner wall of a human organ to be embedded therein so that the whole artificial blood vessel A is fixed to the human organ. Therefore, after the artificial blood vessel A has been implanted in the human organ, the thorns $12a_1$ effectively prevent displacement of the artificial blood vessel A, which may cause the vessel A to be carried by blood flow downstream in the blood vessel. As each of the thorns $12a_1$ is formed by curving a wire into a loop, crossing both end portions of the wire, and fixing the crossed parts with a string or the like, the thorns $12a_1$ can be formed with ease and remain reliable in use for a long time, even though the intermediate wire rings 12 are made of a material which is difficult to weld.

On the other hand, by using the device C for introducing artificial blood vessels in accordance with the invention, the artificial blood vessel A can be smoothly introduced into the catheter 8. In particular, the artificial blood vessel A is inserted into the cartridge 6 by opening the check valve 55 as far as the artificial blood vessel A reaches a position so that it is completely contained therein. Before or after the above insertion, the cartridge 6 is attached to the attachment 5 provided at the open end 8a of the catheter 8, and then the artificial blood vessel A is pulled forward farther so as to be introduced into the catheter 8 through the attachment 5. In this case, when the check valve 55 in the attachment 5 is opened, the check valve 65 of the cartridge 6 is closed, so that blood flowing into the cartridge 6 is prevented from flowing outside the body through the cartridge 6 without fail. In addition, if the artificial blood vessel A is inserted directly into the catheter 8, the artificial blood vessel A cannot be inserted smoothly because the catheter 8 and the artificial blood vessel A are flexible, and the catheter 8 is likely to be bent by the force applied to the catheter 8 or the artificial blood vessel A, thereby to block the path of the artificial blood vessel A or to damage the catheter 8 itself. However, in this embodiment, as the artificial blood vessel A is to be inserted into the catheter 8 through the attachment 5 and the cartridge 6, the attachment 5 and the cartridge 6 are made relatively strong and easy to handle, so that the catheter 8 will not be broken, thereby to enable the artificial blood vessel A to be introduced into the catheter 8 smoothly with ease. In this case, as the bore diameter $d_1$ of the attachment 5 of the catheter 8 is made bigger than the bore diameter $d_3$ of the open end 8a of the catheter 8 and the bore diameter $d_2$ of the front end portion of the cartridge 6 is smoothly connected to the bore diameter $d_3$ of the open end 8a of the catheter 8 when the cartridge 6 is attached to the-attachment 5, the artificial blood vessel A can be prevented from being swollen in the attachment 5 and caught therein, so that the artificial blood vessel A can be introduced directly deeper into the catheter 8.

Figure 28:
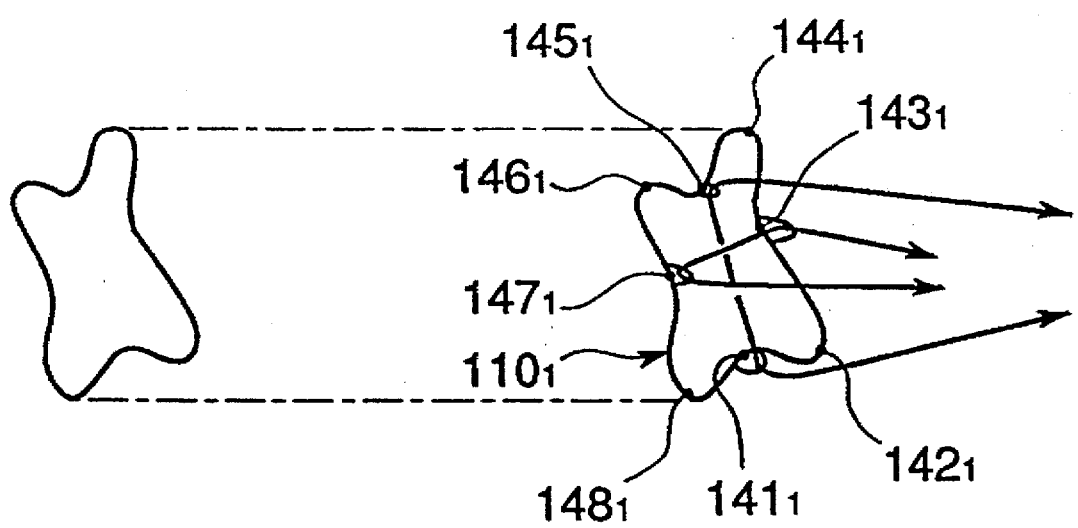
FIG. 28 shows the principle of another embodiment of the invention.
Figure 29:
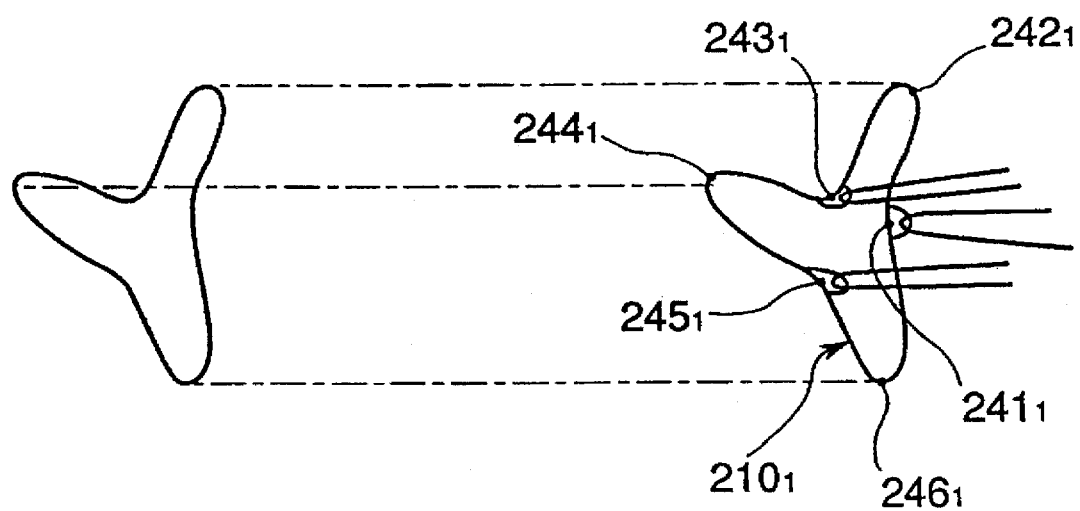
FIG. 29 shows the principle of a different embodiment of the invention.

The invention is not limited to the above-mentioned embodiments. For example, in the above embodiment, the front end wire ring $10_1$ has its circumference divided into two equal arcs to set two dividing points $41_1$, $43_1$ and the two midpoints $42_1$, $44_1$. As shown in FIG. 28, four dividing points $141_1$, $143_1$, $145_1$, $147_1$ and four midpoints $142_1$, $144_1$, $146_1$, $148_1$ may be set by quadrisecting a front end wire ring $110_1$. As shown in FIG. 29, three dividing points $241_1$, $243_1$, $245_1$ and three midpoints $242_1$, $244_1$, $246_1$ may be set by trisecting a front end wire ring $210_1$.

In the above embodiment, the device B for transporting artificial blood vessels is provided with a pair of strings 4 with loop portions 4a. The strings 4 need not always be provided in a pair. However, the strings provided in a pair are effective because a balanced pulling force can be applied to the artificial blood vessel A. The loop portions 4a may be twisted as a whole.

As the balloon catheter 23 is used in the above embodiment, the device B for transporting artificial blood vessels is incorporated into the balloon catheter 23. If the balloon catheter 23 is unnecessary, the artificial blood vessel A may be introduced into or taken out of the catheter by directly operating the tube 2 of the device B for transporting artificial blood vessels.

Figure 30:
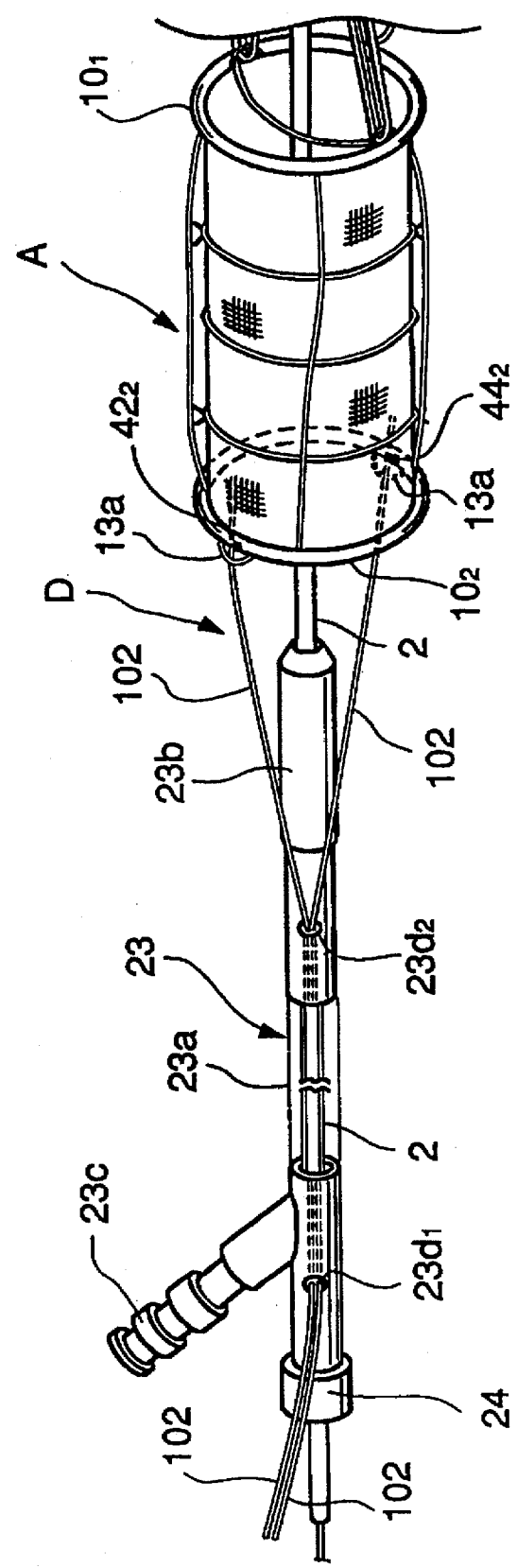
FIG. 30 is a perspective view corresponding to FIG. 12 of a further different embodiment of the invention.

The following method of supporting restoration of the appliance to be implanted is effectively used in the above embodiment. The method is to enable the artificial blood vessel A as the appliance to be implanted to be pulled rearward at the rear end wire ring $10_2$ through the rear loops 13a formed on the rear end wire ring $10_2$ of the artificial blood vessel A at the points $42_2$, $44_2$ corresponding to the midpoints as shown in FIG. 30. In particular, in the above embodiment, for example, the artificial blood vessel A may be mistakenly released at a position off the affected portion 26 shown in FIG. 26. In such a case, when the artificial blood vessel A is pulled backward by operating the device B for transporting artificial blood vessels, the front end wire ring $10_1$ only moves toward the rear end wire ring $10_2$, so that the artificial blood vessel A shrinks in the axial direction thereof and may not be restored to a proper shape. In case the balloon catheter 23 is inserted into the artificial blood vessel A which has been released at a constricted part, the balloon catheter 23 may not be inserted with accuracy into the opening of the rear end wire ring $10_2$ of the artificial blood vessel A but be caught by the peripheral edge of the opening, and the rear end wire ring $10_2$ is pushed toward the front end wire ring $10_1$ and shrinks in the axial direction thereof, so that the artificial blood vessel A may not be restored to a proper shape. Once this happens, the above-mentioned device B for transporting artificial blood vessels can no longer be an effective means for correcting the shrinkage of the artificial blood vessel A or pulling it back to where it should have been end wire ring forward.

In such a case, it is effective to use both a method of and a device for pulling the artificial blood vessel A back to the proper position after it has been released.

Figure 31:
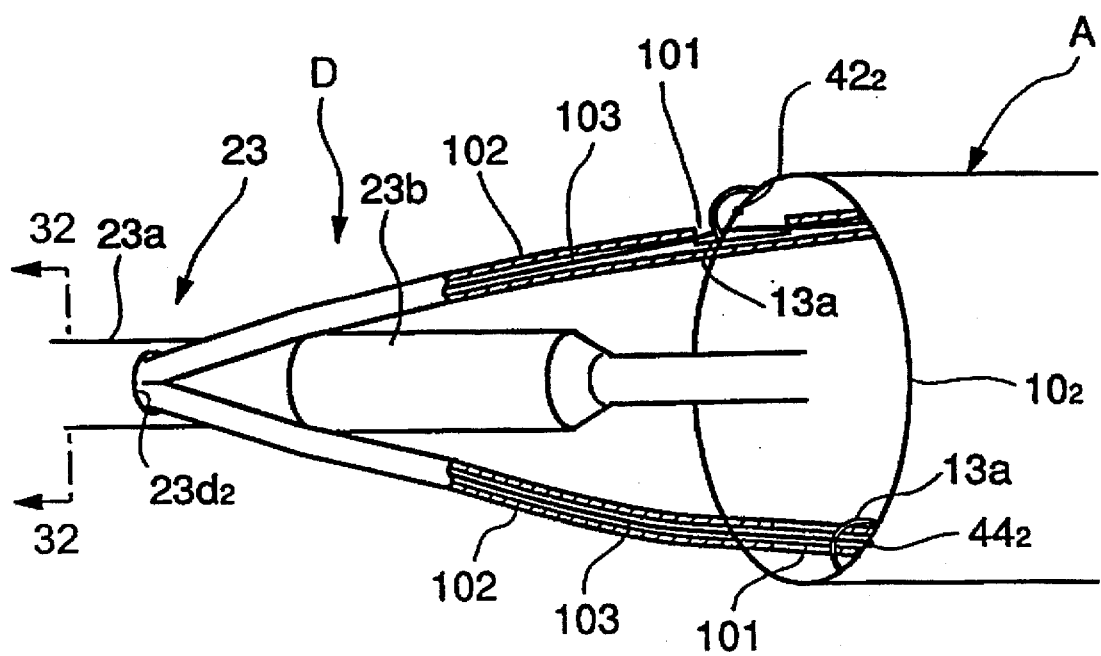
FIG. 31 is an enlarged perspective view of part of the above embodiment.
Figure 32:
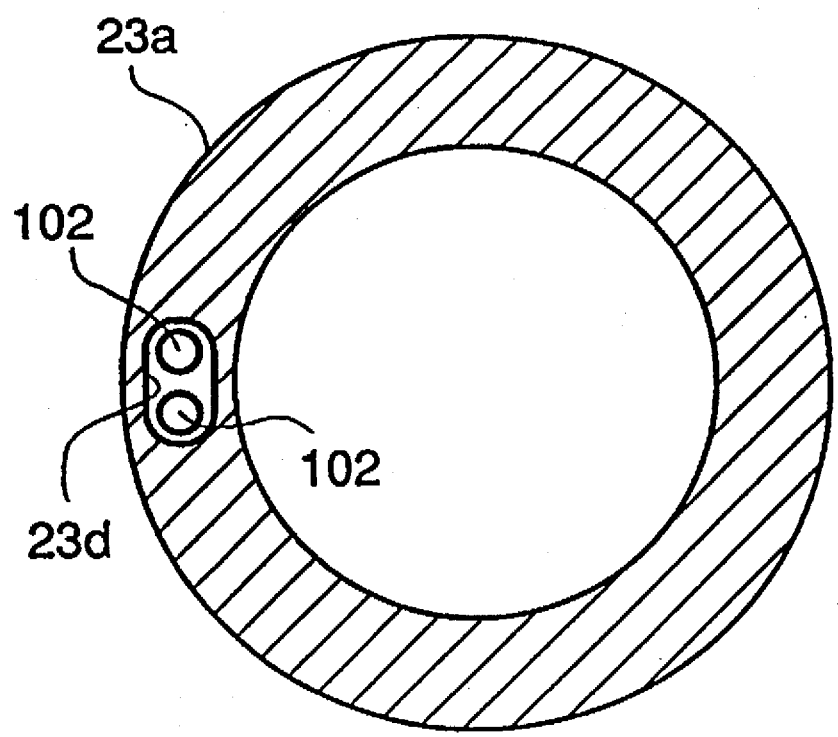
FIG. 32 is an enlarged cross-sectional view along the line Z—Z in FIG. 31.

FIGS. 30 and 31 show a device D for helping restoration for the above purpose, which comprises a pair of tubes 102 each of which is provided with a side window 101 near its front end, and a pair of wires 103 each of which is inserted into one of the tubes 102. Rear loops 13a are formed at the points $42_2$, $44_2$ on the rear end wire ring $10_2$ corresponding to the midpoints, and the rear loops 13a are directly hooked by the wires 103 which have been pulled out of the tubes 102 through the side window 101, and the rear loops 13a are held by the wires 103 by inserting the wires 103 into the tubes 102 again. Then the tubes 102 each of which contains the wire 103 are introduced into the catheter 8 together with the artificial blood vessel A. In particular, a bore 23d oblong in transverse section is formed in the wall of the pipe 23a of the balloon catheter 23 used in the above embodiment to extend along the length of the pipe from the rear end thereof to near the balloon 23b as shown in FIG. 32. An open window $23d_1$ is formed at the rear end of the bore 23d, into which a pair of tubes 102 are introduced through the window $23d_1$ and drawn out through an open window $23d_2$ formed at the forward end of the bore 23d. The tubes 102 can be moved together with the balloon catheter 23 longitudinally when the balloon catheter 23 is pulled forward, and they can also be move relative to the balloon catheter 23 longitudinally when the tubes 102 alone are operated. The device D for helping restoration is used when the position of the artificial blood vessel A is to be adjusted after it has been released as shown in FIG. 26, or when the balloon catheter 23 is inserted into the artificial blood vessel A as shown in FIGS. 26 and 27. When the artificial blood vessel A has been released at a position a little ahead of the affected portion 26 as shown in FIG. 26, the tubes 102 containing the wire 103 is pulled rearward to pull back the rear end wire ring $10_2$ thereby to cause the front end wire ring $10_1$ to follow the rear end wire ring $10_2$. When the balloon catheter 23 is inserted as shown in FIGS. 26 and 27, the tubes 102 containing the wires 103 are pulled back to hold the rear end wire ring $10_2$ not to move forward, and the balloon catheter 23 is pushed into the artificial blood vessel A. Then, only the wires 103 which are contained in the tubes 102 are pulled rearward as far as the front end of the wires 103 reaches the side window 101 of the tubes 102, whereupon the rear loops 13a of the artificial blood vessel A are released from the wires 103, so that the artificial blood vessel A is detached from the device D for helping restoration. As a result, the device D for helping restoration as well as the balloon catheter 23 can be withdrawn with only the artificial blood vessel A left in the affected portion 26.

By using these devices jointly, a proper distance between the front end wire ring $10_1$ and the rear end wire ring $10_2$ can always be maintained. Therefore, it is possible to prevent the artificial blood vessel A from being shrunk longitudinally to deform its proper shape, and to complete insertion of the balloon catheter 23 and adjustment of the position of the artificial blood vessel A quickly and accurately.

Figure 33:
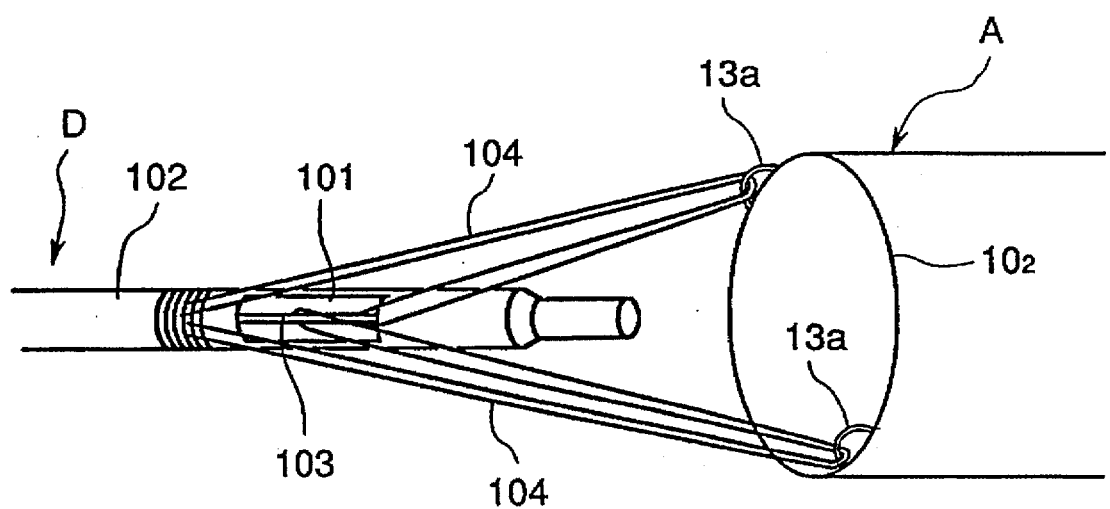
FIG. 33 is a perspective view corresponding to FIG. 31 of a modified form of the embodiment.

The device for helping restoration of the appliance to be implanted can be of a construction shown in FIG. 33. The device is provided near the side window 101 of the tube 102 with a pair of strings 104 each of which has its front end portion formed into a loop. The loop portion of each string 104 is passed through a pair of rear loops 13a and hooked by the wire 103 like the device B for transporting artificial blood vessels. The tube 102 also is contained in the pipe 24a of the balloon catheter 23 and transported like the above-mentioned tube 102.

In the above-mentioned embodiments, in some cases the balloon catheter 23 are not used. In such cases the tube 102 is to be detachably connected with the device for transporting the artificial blood vessel so that the tube and the device can be transported as a unit.

POSSIBLE APPLICATIONS IN INDUSTRY

As mentioned above, the method of collapsing the appliance to be implanted in accordance with the invention is useful to fold the wire rings, which are components of the appliance, into small, regular wavy shapes of the same phase, thereby to collapse the appliance into a small size. The appliance to be implanted in accordance with the invention can be implanted into a target position without fail and has an appropriate construction so as not to hinder the operation of collapsing. The device for introducing the appliance to be implanted into the catheter is useful to introduce the appliance into the catheter without bleeding.

I claim:

1. A method of collapsing an implantable appliance, said appliance including a pair of discrete end wire rings, said end wire rings being interconnected only by a tubular cover made of flexible, tensile sheet and a plurality of intermediate wire rings spaced apart from each other between said end wire rings and circumferentially fixed to said cover, said end wire rings and intermediate wire rings being on the outside of said cover comprising the steps of; pulling said front end wire ring forward against a tapered surface at a plurality of dividing points which equally divide the circumference of said front ring while said tapered surface restrains midpoints between adjacent dividing points from moving forward following the movement of the dividing points so as to fold said front end wire ring into a wavy shape with the dividing points forming forwardly directed peaks and the midpoints forming the bottoms of forwardly directed valleys; and pulling said dividing points of the front wire ring farther forward so as to fold said intermediate wire rings and the rear end wire ring into a wavy shape having the same phase as that of the front end wire ring by the effect of restraint with the tapered surface.

2. The method of collapsing the implantable appliance as described in claim 1 wherein at the dividing points on the front end wire ring, loops are formed and a front pull string passed therethrough.

3. The method of collapsing the implantable appliance as described in claim 2 wherein a common front pull string is passed through the plurality of loops and pulled to gather said dividing points on the front end wire ring toward each other.

4. The method of collapsing the implantable appliance as described in claim 1 wherein a guide robe whose inner surface is tapered with its diameter decreasing toward the front end thereof is provided, said appliance to be implanted is introduced into the guide tube and the dividing points on the front end wire ring are pulled forward to gather said dividing points and said midpoints on each of the wire rings toward each other respectively.

5. The method of collapsing the implantable appliance as described in claim 4 wherein resiliently transformable projections are formed on the tapered surface of said guide tube; and the forward movement of the midpoints on each of the wire rings following the front end wire ring are restrained by contact with the projections so that the midpoints are urged toward each other.

6. The method of collapsing the implantable appliance as described in claim 1 wherein said end wire rings are circumferentially covered with protective material.

7. The method of collapsing the implantable appliance as described in claim 1 wherein said tapered surface is conical.

* * * * *